US008026076B2

(12) United States Patent (10) Patent No.: US 8,026,076 B2
Ruhwald et al. (45) Date of Patent: Sep. 27, 2011

(54) IP-10 BASED IMMUNOLOGICAL MONITORING

(75) Inventors: Morten Ruhwald, Copenhagen (DK); Pernille Ravn, Frederiksberg (DK); Jesper Eugen-Olsen, Hellerup (DK)

(73) Assignee: Hvidovre Hospital, Hvidovre (DK)

( * ) Notice: Subject to any disclaimer, the term of this patent is extended or adjusted under 35 U.S.C. 154(b) by 0 days.

(21) Appl. No.: 12/438,515

(22) PCT Filed: Sep. 5, 2007

(86) PCT No.: PCT/DK2007/000399
§ 371 (c)(1),
(2), (4) Date: Oct. 14, 2009

(87) PCT Pub. No.: WO2008/028489
PCT Pub. Date: Mar. 13, 2008

(65) Prior Publication Data
US 2010/0086950 A1 Apr. 8, 2010

(30) Foreign Application Priority Data

Sep. 5, 2006 (DK) ................................. 2006 01145
Feb. 20, 2007 (DK) ................................. 2007 00262

(51) Int. Cl.
*G01N 33/53* (2006.01)
*G01N 33/569* (2006.01)
(52) U.S. Cl. ...................................... 435/7.24; 435/7.32
(58) Field of Classification Search ........................ None
See application file for complete search history.

(56) References Cited

U.S. PATENT DOCUMENTS

| 4,965,192 | A | 10/1990 | Maes | |
|---|---|---|---|---|
| 7,608,392 | B2 * | 10/2009 | Rothel et al. ...................... | 435/5 |
| 2003/0143641 | A1 | 7/2003 | Brice | |
| 2005/0163746 | A1 * | 7/2005 | Karmon et al. .............. | 424/85.1 |
| 2006/0040329 | A1 * | 2/2006 | Kelvin et al. ................... | 435/7.2 |
| 2006/0051358 | A1 | 3/2006 | Banchereau et al. | |
| 2009/0324503 | A1 * | 12/2009 | Lewinsohn et al. .......... | 424/9.81 |

FOREIGN PATENT DOCUMENTS

| WO | WO 03/063759 A2 | 8/2003 |
|---|---|---|
| WO | WO 2004/042396 A1 | 5/2004 |
| WO | WO 2005/012907 A1 | 2/2005 |
| WO | WO 2007/039400 A1 | 4/2007 |

OTHER PUBLICATIONS

Ananaba, G.A. et al., "Chemokine and Chemokine Receptor Regulation of Th1 Response Against Chlamydia" Abstracts of the General Meeting of the American Society for Microbiology, May 2001, p. 347, vol. 101.

Azzurri, Annalisa et al., "IFN-y-inducible protein 10 and pentraxin 3 plasma levels are tools for monitoring inflammation and disease activity in *Mycobacterium tuberculosis* infection" Microbes and Infection, 2005, pp. 1-8, vol. 7.

Belay, Tesfaye et al., "Chemokine and Chemokine Receptor Dynamics during Genital Chlamydial Infection" Infection and Immunity, Feb. 2002, pp. 844-850, vol. 70, No. 2.

Bourgarit, Anne et al., "Explosion of tuberculin-specific Th1-responses induces immune restoration syndrome in tuberculosis and HIV co-infected patients" AIDS, 2006, pp. F1-F7, vol, 20, No. 2.

Ferrero, Elisabetta et al., "Macrophages exposed to *Mycobacterium tuberculosis* release chemokines able to recruit selected leucocyte subpopulations: focus on yo cells" Immunology, 2003, pp. 365-374, vol. 108, No. 3.

Kremlev, Sergey et al., "Differential expression of chemokines and chemokine receptors during microglial activation and inhibition" Journal of Neuroimmunology, 2004, pp. 1-9, vol. 149.

Lindholm, C. et al., "Induction of Chemokine and Cytokine Responses by *Helicobacter pylori* in Human Stomach Explants" Scandinavian Journal of Gastroenterology, Oct. 2001, pp. 1022-1029, vol. 36, No. 10.

Molesworth-Kenyon, S.J. et al., "Abundant Expression of IP-10 and Mig in the HSV-1 Infected Cornea" Investigative Ophthalmology & Visual Science, Apr. 2004, p. U127, vol. 45.

Nagarajan, Uma M., et al., "*Chlamydia trachomatis* Induces Expression of IFN-y-Inducible Protein 10 and IFN-B Independent of TLR2 and TLR4, but Largely Dependent on MyD88" Journal of Immunology, Jul. 2005, pp. 450-460, vol. 175.

Ruhwald, Morten et al., "CXCL10/IP-10 release is induced by incubation of whole blood from tuberculosis patients with ESAT-6, CFP10 and TB7.7" Microbes and Infection, Jun. 2007, pp. 806-812, vol. 9, No. 7.

Semnani, Roshanak Tolouei et al., "The early response to the infective stage of the filarial parasite *Brugia malayi* is dominated by inflammatory genes in macrophages" FASEB Journal, Mar. 22, 2002, p. A1038, vol. 16, No. 5.

International Search Report dated Mar. 28, 2008 for PCT/DK2007/000399.

Brice, Gary T. et al., "Expression of the chemokine MIG is a sensitive and predictive marker for antigen-specific, genetically restricted IFN-γ production and IFN-γ—secreting cells" Journal of Immunological Methods, 2001, pp. 55-69, vol. 257.

Demissie, Abebech et al., "Healthy Individuals That Control a Latent Infection with *Mycobacterium tuberculosis* Express High Levels of Th1 Cytokines and the IL-4 Antagonist IL-δ2" The Journal of Immunology, 2004, pp. 6938-6943, vol. 28.

Hughes, A. J. et al., "Diagnosis of *Mycobacterium tuberculosis* infection using ESAT-6 and intracellular cytokine cytomery" Clinical and Experimental Immunology, 2005, pp. 132-139, vol. 142.

(Continued)

*Primary Examiner* — David A Saunders
(74) *Attorney, Agent, or Firm* — Knobber Martens Olson & Bear LLP

(57) ABSTRACT

The present invention relates to an immunological method and, more particularly, a method for measuring cell-mediated immune reactivity (CMI) in mammals based on the production of IP-10. The invention further discloses an assay and a kit for measuring CMI to an antigen using whole blood or other suitable biological samples. The methods of the present invention are useful in therapeutic and diagnostic protocols for human, livestock and veterinary and wild life applications, thus the invention further relates to a method for diagnosing an infection in a mammal.

8 Claims, 5 Drawing Sheets

OTHER PUBLICATIONS

Figure 1:
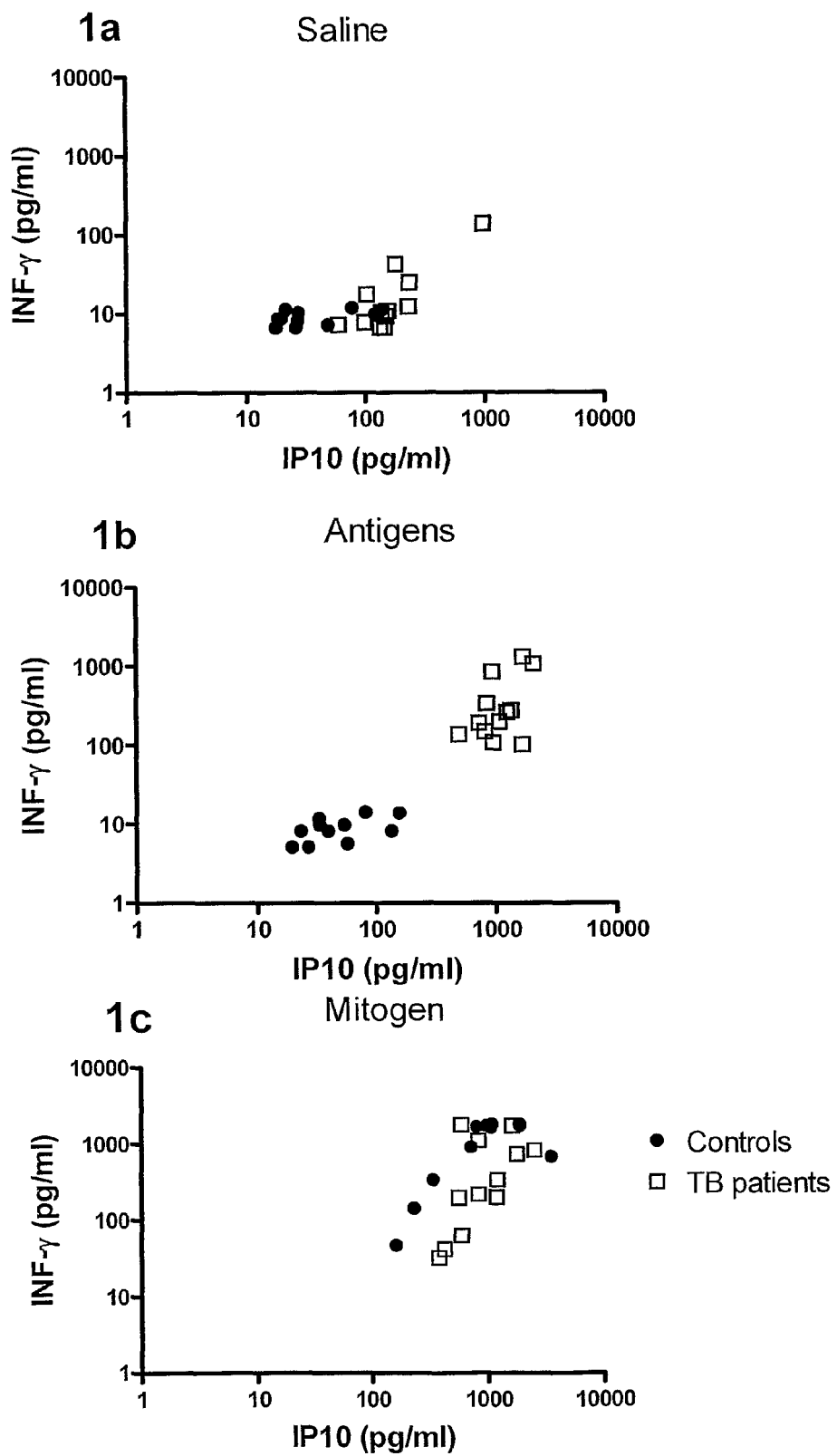

Madhukar, Pai et al., "Serial Testing of Health Care Workers for Tuberculosis Using Interferon-γ Assay" American Journal of Respiratory and Critical Care Medicine, 2006, pp. 349-355, vol. 174.

Uicker, William C. et al., "Cytokine and chemokine expression in the central nervous system associate with protective cell-mediated immunity against *Cryptococcus neoformans*" Medical Mycology, Feb. 2005, pp. 27-38, vol. 43.

Ulrichs, Timo et al., "Differential T cell responses to *Mycobacterium tuberculosis* ESAT6 in tuberculosis patients and healthy donors" Eur. J. Immunol., 1998, pp. 3949-3958, vol. 28.

Lein, A. David et al., "In Vitro Cellular and Cytokine Responses to Mycobacterial Antigens: Application to Diagnosis of Tuberculosis Infection and Assessment of Response to Mycobacterial Vaccines" The American Journal of the Medical Science, Jun. 1997, pp. 364-371, vol. 313, No. 6.

Okamoto, Masakazu et al., "Evaluation of interferon-y, interferon-y-inducing cytokines, and interferon-y-inducible chemokines in tuberculous pleural effusions" J Lab Clin Med, Feb. 2005, pp. 88-93, vol. 145, No. 2.

Abramo, Clarice et al., "Monokine induced by interferon gamma and IFN-γ response to a fusion protein of *Mycobacterium tuberculosis* ESAT-6 and CFP-10 in Brazilian tuberculosis patients" Microbes and Infection, 2006, pp. 45-51, vol. 8.

* cited by examiner

IP-10 BASED IMMUNOLOGICAL MONITORING

CROSS REFERENCE TO RELATED APPLICATION

This application claims the benefit and priority to and is a U.S. National Phase of International Application Number PCT/DK2007/000399, filed on Sep. 5, 2007, designating the United States of America and published in the English language, which is an International Application of and claims the benefit of priority to Danish Patent Application No. PA200601145, filed Sep. 5, 2006, and Danish Patent Application No. PA200700262, filed Feb. 20, 2007. The disclosures of the above-referenced applications are hereby expressly incorporated by reference in their entireties.

FIELD OF INVENTION

The present invention relates generally to an immunological assay and, more particularly, an assay for measuring cell-mediated immune reactivity (CMI). Even more particularly, the present invention provides an assay and a kit for measuring a cell-mediated response to an antigen using whole blood or other suitable biological samples. The assay is useful in therapeutic and diagnostic protocols for human, livestock and veterinary and wild life applications.

Measurement of cell-mediated immune responses is important for immune diagnosis of many infectious and autoimmune diseases, as a marker for immunocompetence, and for detection of T-cell responses to endogenous and exogenous antigens (i.e. infections and vaccines).

The present invention provides a method for measuring CMI in a mammal by incubating a sample from the mammal which comprises T-cells or other cells of the immune system with an antigen. Production of IP-10 is then detected. The presence or level of immune effecter is then indicative of the level of cell mediated responsiveness of the subject.

BACKGROUND OF THE INVENTION

Tuberculosis

The discovery of mycobacterium tuberculosis (MTB)-specific immunodominant antigens has led to a significant new avenue for the diagnosis of tuberculosis (TB). Early work had shown the potential to replace the Tuberculin Skin Test (TST) by a test that assayed the in vitro production of interferon gamma (IFN-γ) by T cells in response to defined MTB antigens. Around the same time, a major advance was the discovery of the highly immunogenic antigens, early secreted antigenic target 6 (ESAT-6) and culture filtrate protein 10 (CFP-10) and TB7.7 that improved specificity significantly. These antigens are encoded within the region of difference 1 (RD1) of the pathogen and are consequently absent from all Bacille Calmette Guerin (BCG) vaccine strains and most non-tuberculous mycobacteria (exceptions include Mycobacterium kansasii, Mycobacterium marinum Mycobacterium szulgai). IFN-γ responses to overlapping peptides of the RD1 encoded antigens ESAT-6, CFP-10, TB7.7 form the basis for the detection of MTB infection in two licensed and commercially available tests.

QuantiFERON-TB Gold (Cellestis Limited, Carnegie, Victoria, Australia), a whole blood enzyme-linked immunoassay (ELISA) has European CE mark approval and recently received American Food and Drug Administration (FDA) approval for the detection of both latent TB infection and disease.

T-SPOT.TB (Oxford Immunotec, Oxford, UK), an enzyme-linked immunospot assay (ELISPOT) that uses peripheral blood mononuclear cells has European CE mark approval and was approved for use in Canada in 2005. T-SPOT.TB only uses ESAT-6 and CFP10.

However, the limitations of the currently available tests are:
1) The sensitivity may be impaired in immunosuppressed individuals (such as HIV positive or patients receiving immunosupressing medication),
2) In some situations a relatively large volume of blood is necessary (3 ml per QuantiFERON test and 8 ml for the T-SPOT.TB), which may limit its use in infants and severely ill and anaemic children,
3) The tests do not discriminate between active, latent and recent infection
4) The tests have not been demonstrated to be able to predict who will progress from recent or latent TB to active TB.

Most of the test limitations are due to measurement of the effect parameter IFN-γ at very low levels, close to the limit of even the most sensitive method (in the QuantiFERON test down to 0.35 IU/ml (17.5 pg/ml) and in the T-SPOT.TB 5 spots/field). Decreasing cut-off to enhance sensitivity will eventually result in impaired specificity of the tests. A recent publication based on the QuantiFERON test has shown that that repeated testing of people with test results in the lower range of IFN-γ varies around the cut-off level which underlines the potential risk of false positive and false negative results of the QuantiFERON (QFT) test (Pai, M. et al).

To overcome the evident fragility of the tests, sensitivity could be improved by using additional M. tuberculosis specific antigens and this has been done in the third generation of the QuantiFERON tests (QFT), the QuantiFERON In tube test (QFT-IT) which now comprises an additional antigen named TB7.7(p4) and potentially sensitivity is improved, but it still depends on measurements at very low IFN-γ levels.

This approach has been tried by others, i.e. recently is was shown that the Monokine Induced by IFN-γ (MIG/CXCL9) was specifically expressed in vitro after stimulation with M. tuberculosis specific antigens (ESAT-6/CFP10) and PPD. The sensitivity of CXCL9, however was very low and lower than that of IFN-γ. Another smaller study based on intracellular cytokine cytometry in CD4+ T cells following ESAT-6 stimulation, tested if expression of IFN-γ, IL-2, IL-4, IL-10 or the activation marker CD40L could distinguish TB from non-TB disease. None of these markers were found to be comparable or superior to IFN-γ (Abramo C, et al) (Hughes, A. et al).

Yet no sensitive and specific markers to replace IFN-γ for diagnosis of TB infection have been identified in the presently published literature. Various have disclosed IP-10 in connection to infections, but not as a marker in the diagnosis of infection with a prior antigen stimulation.

Chlamydia

The diagnosis of genital chlamydial infections evolved rapidly from the 1990s. Nucleic acid amplification tests (NAAT), such as polymerase chain reaction (PCR), transcription mediated amplification (TMA), and the DNA strand displacement assay (SDA) now are the mainstays. The most commonly used and widely studied chlamydia NAATs in the US and many other industrialized countries are Aptima (Gen-Probe), Probe-Tec (Becton-Dickinson), and Amplicor (Roche). The Aptima Combo II assay tests simltaneously for C. trachomatis and Neisseria gonorrhoeae, the cause of gonorrhea. NAAT for chlamydia may be performed on swab specimens collected from the cervix (women) or urethra (men)

At present, the NAATs have regulatory approval only for testing urogenital specimens. The NAATs have largely replaced culture, the historic gold standard for chlamydia diagnosis, and the non-amplified probe tests, such as Pace II (Gen-Probe). The latter test is relatively insensitive, successfully detecting only 60-80% of infections in asymptomatic women, and occasionally giving falsely positive results. Culture remains useful in selected circumstances and is currently the only assay approved for testing non-genital specimens.

Chlamydia diagnosis is thus based on complicated and resource demanding technology such as PCR, not readily available in the developing world. A fast and easy technology would improve diagnostic measures for this important disease, CA 2,478,138 discloses that elevated blood levels of the chemokine CXCL10 polypeptide are associated with respiratory illnesses (e.g. SARS, influenza and community-acquired pneumonia) and are useful in diagnosis of patients. Methods are provided for diagnosis and treatment of patients suffering from respiratory illnesses.

WO 05/091969 discloses markers for TSE (Transmissible Spongiform Encephalopaties) that are present prior to formation of detectable pathological prion protein are useful to detect this infection prior to clinical signs. IP-10 is just one of several markers disclose and this application does not disclose any antigen stimulation.

US2004-038201 discloses distinct gene expression programs activated in response to different pathogens in macrophages. IP-10 is again just one in many markers mentioned and this application does not disclose any antigen stimulation.

Annalisa Azzurri et al. discloses IFN-γ-inducible protein 10 and pentraxin 3 plasma levels are tools for monitoring inflammation and disease activity in Mycobacterium Tuberculosis infection. The article shows that IP-10 plasma level is spontaneously increased in patients with TB, again this reference does not disclose any antigen stimulation.

WO 03/063759 discloses a method of identifying a heat shock protein (Hsp) derived peptide useful for diagnosis or therapy. The effect of the compounds of this invention was tested on pheripheral blood monocytes by measuring the IP-10 level in response to subsequent stimulation with LPS. Direct stimulation with the test compounds without subsequent stimulation with LPS, did not give rise to an increase in the IP-10 level.

WO 07/039400 discloses a method and kit for the diagnosis of Immune Restoration Syndrome which is associated with tuberculosis (TB-IRS) in patients infected with tuberculosis as well as HIV/TB co-infected patients. In order to diagnose TB-IRS the inventors detected the level of Th1 response against PPD and/or a 16 KDA protein in comparison to the Th1 response against ESAT-6, CFP-10, 85B (negative control) and used a rise in the Th1 response as an indicative of TB-IRS.

To overcome the problems of impaired sensitivity and low levels of detectable IFN-γ by the currently available tests using antigen stimulation, the present inventors suggest the use of an alternative biomarker than IFN-γ.

SUMMARY OF THE INVENTION

The present invention proposes a novel diagnostic principle. A test system that can detect infection with e.g. tuberculosis leishmania or chlamydia, based on measuring the chemokine IP-10 following stimulation of immune cells with antigenic proteins/peptides.

The described test system IP-10 is more sensitive than tests based on IFN-γ as effect parameter, it improves testing and diagnosing. The test can be performed using lower amounts of blood because the samples can be diluted at time of incubation or before analysis. The test can be performed at shorter incubation times. Furthermore, the test system may allow discriminating between various stages of infection such as e.g. active, recent and latent TB infection.

In short the present invention can be described as an immunological method comprising the steps of incubating a sample obtained from a mammal with at least one antigen, determining the IP-10 level in said sample and comparing said determined IP-10 level with a reference-level, thereby determining whether mammal has previously encountered the antigen generating immunological reactivity to the antigen, or previously encountered other antigens generating immunological cross reactivity to the antigen.

DETAILED DESCRIPTION

The present invention provides an assay of the potential or capacity of a subject to mount a CMI response. The assay is based on measuring immune effecter molecule production by cells of the immune system in response to antigenic stimulation. The immune effecters may be detected using ligands such as antibodies specific for the effecters or by measuring the level of expression of genes encoding the effecters.

The present invention provides, therefore, means to determine the responsiveness of CMI in a subject and, in turn, provides means for the diagnosis of infectious diseases, pathological conditions, level of immunocompetence and a marker of T-cell responsiveness to endogenous or exogenous antigens One aspect of the invention relates to an assay of the potential or capacity of a subject to mount an IP-10 response. The assay is based on measuring IP-10 production by cells of the immune system in response to antigenic stimulation. The IP-10 production may be detected using ligands such as antibodies specific for IP-10 or by measuring the level of expression of genes encoding IP-10. The present inventors have demonstrated the test principle using two different types of infection: Tuberculosis and Chlamydia. In the case of tuberculosis a test based on *M. Tuberculosis* specific stimulation and subsequent determination of IP-10, can identify persons infected with *M. tuberculosis*. In the case of Chlamydia a test based on stimulation with *C. Trachomatis* extract can identify persons infected with Chlamydia.

The described test system measures higher levels of the biomarker IP-10, than the levels of IFN-γ, the marker the currently available assays are based on. The test system based on IP-10 is as specific as and more sensitive than tests based on e.g. IFN-γ as effect parameter, it improves testing and diagnosing of immunocompromised individuals (Example 10), the test can be performed using lower amounts of blood because the samples can be diluted at time of incubation or before analysis (Examples 9 and 13). It also improves the speed of diagnosis, as IP-10 is produced in significant amounts after few hours of incubation as shown in example 11. In the case of tuberculosis, the test system may allow discriminating between active, recent and latent TB infection and, in addition the test system is potentially capable of identifying persons at risk of progressing to active TB. The test system is based on IP-10 detection using an immunoassay (i.e. ELISA or Luminex) and the test system can potentially be developed into a field friendly immunochromatographic test applicable in low resource settings, where the test result is presented by a colour reaction detectable to the naked eye.

The assay described in the present invention solves a series of problems. The currently available assays measure the effect parameter IFN-γ at very low levels, close to the limit of even the most sensitive detection method (in the case of tuberculosis tests, the QuantiFERON test has a cut-off level for positive test at 0.35 international units/ml (17.5 pg/ml) and in the T-SPOT.TB test 5 spot forming units/field). Decreasing cut-off to enhance sensitivity will eventually result in impaired specificity of the tests. Publications based on the Quantiferon test have shown that that repeated testing of people with test results in the lower range of IFN-γ varies around the cut-off level which underlines the potential risk of false positive and false negative results of the Quantiferon (QFT) test. In addition the current test may give false negative results in immunosuppressed individuals who are unable to mount an IFN-γ response above the cut-off level. As the amount of IP-10 release is much higher after antigen stimulation when compared to IFN-γ: the sensitivity is higher, fewer tests are deemed false negative, test results are more reproducible, and, less indeterminate test results are expected in immunosuppressed individuals.

Furthermore, because antigen induced IP-10 is secreted in such high concentrations it is possible to dilute the sample before or after the incubation step. This means that the amount of sample material (e.g. whole blood) needed to perform the test can be reduced e.g. in the case of whole blood down to or even at or below 0.25 ml, such as 0.20 ml, e.g. 0.15 ml, such as 0.1 ml, e.g 0.05 ml. In a preferred embodiment the test can be performed down to or even below 0.1 ml. Thus a "mini assay" suitable for patients with low blood volume (e.g. children/infants or anaemics) can be developed. Furthermore, using e.g. blood from e.g. a finger-prick, the mini assay can be made even more user friendly as vein puncture is avoided.

Furthermore, in the case of tuberculosis none of the currently available tests can discriminate between Active and Latent infection. Surprisingly the inventors found the concentration of IP-10 in the un-stimulated, but incubated sample material i.e. the nil sample (e.g. whole blood), is higher among patients with active disease compared to healthy individuals with latent disease. The present inventors propose that the IP-10 concentration in sample material incubated with an inactive solution (Nil) in combination with an antigen-specific test can be used as marker for active infection (e.g. tuberculosis) versus latent infection (e.g. tuberculosis).

The Assay

Thus, one aspect of the present invention relates to an immunological method comprising the steps of
  a) incubating a sample obtained from a mammal with at least one test-antigen
  b) determining the IP-10 level in said sample
  c) comparing said determined IP-10 level with a reference-level, thereby determining whether mammal has previously encountered the test-antigen generating immunological reactivity to the test-antigen or previously encountered other antigens generating immunological cross reactivity to the test-antigen.

It is to be understood that any of the methods described in the present invention is platform independent. Accordingly, any immunological method such as but not limited to ELISA, Luminex, Multiplex, Immunoblotting, TRF-assaýs, immunochromatographic lateral flow assays, Enzyme Multiplied Immunoassay Techniques, RAST test, Radioimmunoassays, immunofluorescence and various immunological dry stick assays (e.g. cromatographic stick test) may be applicable to the present invention.

In a second aspect, the present invention relates to a method for diagnosing an infection, said method comprising the steps of
  a) incubating a sample obtained from a mammal with at least one test-antigen under the proviso that said test-antigen is not PPD or LPS
  b) determining the IP-10 level in said sample
  c) comparing the determined IP-10 level with a reference-level, thereby determining whether said mammal is infected with a micro organism, if the determined IP-10 level is above the reference-level.

The present inventors have demonstrated that direct stimulation with the selected test-antigen(s) or antigen(s) for evaluation is sufficient to obtain a readout that enables the skilled addressee to conclude whether the sample has encountered the test-antigen(s) generating immunological reactivity to the test-antigen(s) or previously encountered other test-antigens generating immunological cross reactivity to the chosen test-antigen(s).

Thus, in one embodiment, the present invention also relates to immunological methods as described herein, wherein any further or subsequent stimulation is excluded.

Subsequent or further stimulation may cover any type of stimulation e.g. priming or stimulating a sample with a biological inactive substance or a substance with a biological effect related to the inflammatory response, such as but not limited to mitogens, bacterial products or biological active proteins.

Thus, in one embodiment, the present invention relates to immunological methods as described herein, wherein any further or subsequent stimulation with LPS is excluded.

Accordingly, said method is applicable for the detection of an infection in e.g.

people who is in high risk of developing infectious diseases such as but not limited to Tuberculosis, Chlamydia, Leishmania, Trypanosoma and Schistosoma.

The present invention also relates to a method according to the present invention, wherein the sample is divided into at least 2 fractions and
  a) incubating the first fraction of the sample with the test-antigen(s) to generate a response sample
  b) incubating the second fraction of the sample with an inactive solution to generate a nil sample
  c) determining the IP-10 level in the two fractions
  d) determining the antigen-dependent IP-10 response of the sample by subtracting the IP-10 level determined in the nil sample from the IP-10 determined in the response sample
  e) comparing the test-antigen-dependent IP-10 response or a value derived thereof with the reference-level or a value derived thereof,
thereby determining whether mammal has previously encountered the test-antigen(s) and thus generate immunological reactivity to the test-antigen(s) or previously encountered other antigens generating immunological cross reactivity to the test-antigen(s) and/or is going to develop infection.

In one embodiment the assay performance can be potentiated by concomitant addition of an immunostimulatory molecule with the antigen selected for evaluation, said immunostimulatory molecule being a cytokine selected from the non-limiting group consisting of IL-2, IL-12, TNF-α, and IFN-γ.

In another embodiment the immunostimulatory molecule is a soluble receptor (e.g. di- or polymere of the B7 molecules (CD80/CD86)) or an antibody (e.g. an CD28-binding antibody).

In another embodiment the immunostimulatory molecule has the property of providing T cells a co-stimulatory signal (known to those skilled in the art as the signal 2), said co-stimulatory signal is unable to induce an IP-10 response alone but will increase the IP-10 response if the cells generate an CMI response to the antigen selected for evaluation.

In another embodiment potentiating the assay can be achieved by inhibiting anti-inflammatory processes occurring during the incubation step. In one embodiment the assay can be potentiated with inhibiting antibodies or soluble receptors that bind anti-inflammatory molecules such as but not limited to IL-4, IL-10 and TGF-β.

In another embodiment potentiating the assay can be achieved by inhibition of anti-inflammation mediated through inhibition or elimination of cell populations acting inhibitory to the CMI response such as regulatory T-cells.

Specifically as used herein the term Purified Protein Derivative (PPD or tuberculin) is a precipitate of non-species-specific molecules. PPD or tuberculin is obtained by extracting proteins from a mixture of *M. tuberculosis* or other mycobacteria such as M. avium. PPD is commonly employed in testing for the presence of cellular immunity or Th1 response generated either against BCG or against M. tuberculosis. For example, it can be obtained from the TubersolB of Connaught Laboratories Limited prepared from a large Master Batch, Connaught Tuberculin (CT68), or in the form of RT23 obtained from the Statens Serum Institute (SSI, Copenhagen Denmark).

The ESAT-6 protein (early secreted antigenic target 6) is a major secreted antigen which has been purified from *M. tuberculosis* short-term culture filtrates. As referred herein ESAT-6, CFP-10(culture filtrate protein 10) and 85B can be obtained from cell lysate and purification, by recombinant techniques or produced as synthetic peptides. For example ESAT6 can be obtained as a recombinant protein from Statens Serum Institute.

Tuberculin or PPD (purified protein derivative) differs from ESAT-6, (early secreted antigenic target 6) CFP-10 (culture filtrate protein 1O), and TB7.7 which are encoded by genes (in the RD-1 region) located only within the *M. tuberculosis* genome and are not contained in BCG (the Bacille of Calmette et Guérin). It differs from PPD because PPD is also contains other antigens that are shared with e.g. BCG substrains and with several non-tuberculous mycobacterial species with low or no pathogenicity.

Optionally, the method may further comprise dividing the sample into 3 fractions and incubating the third fraction of the sample with a T cell activator to generate a positive control. Here immune cells may be incubated in e.g. three separate populations: nil control (e.g. saline), Ag stimulated (e.g. Chlamydia or tuberculosis specific proteins or derivates hereof) and positive control (e.g. Phytohemagglutinin). Immune cells can be in the form of whole blood, diluted whole blood or various purifications of cell population like peripheral blood mononuclear cells, monocytes or T cells. The cells can be obtained from blood, urine, pleural fluid, bronchial fluid, oral washings, tissue biopsies, ascites, pus, cerebrospinal fluid, aspirate, and/or follicular fluid. Immune cells incubate for e.g. 4-24 h at 37° C.

In one embodiment, the sample is divided into at least 2 fractions and
 a) incubating the first fraction of the sample with the antigen to generate a response sample
 b) incubating the second fraction of the sample with an inactive solution to generate a nil sample
 c) determining the IP-10 level in the two fractions
 d) determining the antigen-dependent IP-10 response of the sample by subtracting the IP-10 level determined in the nil sample from the IP-10 determined in the response sample
 e) comparing the antigen-dependent IP-10 response or a value derived thereof with the reference-level or a value derived thereof,
 f) comparing the antigen spontaneous IP-10 response or a value derived thereof with the reference-level or a value derived thereof,
thereby determining whether mammal has previously encountered the antigen and thus generate immunological reactivity to the antigen or previously encountered other antigens generating immunological cross reactivity to the antigen and thereby determining whether the mammal has an active, a recent, or a latent infection if mammal is responding to treatment, or is going to develop infection.

More specifically, the sample is divided into at least 3 fractions and
 a) incubating the first fraction of the sample with the antigen to generate a response sample
 b) incubating the second fraction of the sample with an inactive solution to generate a nil sample
 c) incubating the third fraction of the sample with a stimulatory solution (e.g. PHA) to generate a mitogen sample
 c) determining the IP-10 level in the three fractions
 d) determining the antigen-dependent IP-10 response of the sample by subtracting the IP-10 level determined in the nil sample from the IP-10 determined in the response sample
 e) comparing the antigen-dependent IP-10 response or a value derived thereof with the reference-level or a value derived thereof,
 f) determining the mitogen dependent IP-10 response of the sample by subtracting the IP-10 level determined in the nil sample from the IP-10 determined in the mitogen sample
 g) comparing the mitogen dependent IP-10 response or a value derived thereof with the reference-level or a value derived thereof,
 h) comparing the antigen spontaneous IP-10 response or a value derived thereof with the reference-level or a value derived thereof,
thereby determining whether mammal has previously encountered the antigen and thus generate immunological reactivity to the antigen or previously encountered other antigens generating immunological cross reactivity to the antigen and thereby determining whether the mammal has an active, a recent, or a latent infection, or if mammal is responding to treatment, is going to develop infection, or is immune-suppressed.

The term "mitogen" refers to any chemical or chemical composition promoting cell division. Mitogens may act upon both T cells and B cells either separately or simultaneously. Accordingly, the term mitogen also covers the terms T cell-activator and B cell-activator, and is thus used herein interchangeably. The mitogens of the present invention covers all mitogens known by the skilled person such as but not limited to phytohaemagglutinin (PHA), concanavalin A (conA) lipopolysaccharide (LPS) and pokeweed mitogen (PWM). In a preferred embodiment of the present invention the mitogen is a T-cell activator and even more preferably the mitogen is PHA. In another preferred embodiment of the present invention the mitogen is a monocyte/macrophage activator. IP-10 production is then determinate by any cytokine or chemokine detection method known to the skilled addressee such as but not limited to antibody-based technologies e.g. xMAP, multiplexing, Luminex, ELISA, ELISPOT, lateral stick assay or mRNA based techniques like Real time polymerase chain reaction (RT-PCR) or Intracellular flow cytometri (IC-FACS).

The quantity of IP-10 in response to antigens (e.g. Chlamydia extract antigens or tuberculosis specific proteins or derivatives hereof) may be determined by subtracting the background production of IP-10 and the probable infection with e.g. *M. tuberculosis* is interpreted on the basis of this antigen-specific IP-10 response.

The tuberculosis data in the present application is developed using existing technology: QuantiFERON® TB-Gold In-Tube test (Cellestis, Carnegie, Australia), in which whole blood is drawn directly into vacutainer tubes pre-coated with either saline (nil), TB specific peptide antigens (Ag) or mitogen (PHA). The tubes were incubated in a presently preferred embodiment at 18 h at 37° C., where after cytokine concentration was measured by xMAP technology on the Luminex platform (Luminex Corporation, USA), using Biosource reagents (Biosource Camarillo USA), and was thus able to switch the effect parameter from the traditional parameter IFN-γ to IP-10, which is expressed in higher concentrations and performs better.

The high sensitivity of the present invention makes this method an excellent tool for differentiating between active infection, latent infection, recent infection, infection in a child/newborn and/or long term latent infection. Thus in one embodiment, the present invention relates to a method wherein an antigen-dependent IP-10 response above the reference-level together with a nil indicates that the mammal has an active infection, a latent infection, a recent infection, and/or a long term latent infection.

In another embodiment the present invention relates to a method where the amount of sample material (e.g. whole blood) used in the test is reduced. In the case of whole blood down to the range of 3 to 0.1 ml, and in the case of PBMCs the cell number is in the range of $1\times10^6$ to $0.05\times10^6$. This "mini assay" suitable for patients with low blood volume (especially children/infants or patients with anaemia) is innovative because it can diagnose a disease (e.g. tuberculosis) without haemodynamic consequences for the donor or be performed on a very scarce sample material e.g. cells from spinal fluid, pleural fluid or blood from the umbilical cord.

Combination with Other Markers

Measuring IP-10 in combination with one or more of the following markers may reduce the number of false positive and increase the discriminatory power. Thus, in one embodiment, the method further comprises,
 a) determining the level of IP-10 and MCP-1 in response to the antigenic stimulation,
 b) combining the determined level of IP-10 and MCP-1, and
 c) comparing said combined level with a combined reference-level.

As understood by the skilled addressee the combined reference-level is determined by measuring the IP-10 level and any of the suggested combinatorial markers such as but not limited to MCP-1 level in a healthy population and combining said determined IP-10 and MCP-1 level by means of arithmetic such as but not limited to addition. The combined reference-level is determined at a selected cut-off point related to the distribution of the combined reference-level e.g. mean+2 standard deviations in a healthy population or by other means known to the skilled addressee.

Further combinatorial markers comprises IL-2 and INF-γ.

In one embodiment, the present invention discloses a method which further comprises
 a) determining the level of INF-γ and optionally MCP-1 and/or IL-2 in response to the antigenic stimulation,
 b) combining the determined level of IP-10 and INF-γ and optionally MCP-1 and/or IL-2, and
 c) comparing said combined level with a combined reference-level.

In one embodiment, the method comprises,
 a) determining the level of IP-10 in response to the antigenic stimulation,
 b) comparing the level of IP-10 to a reference level or a value derived thereof
 c) determining whether said mammal has previously encountered said antigen and thus generated IP-10 reactivity to the antigen
 d) determining the level of MCP-1 in response to the antigenic stimulation,
 e) comparing the level of MCP-1 to a reference level or a value derived thereof
 f) determining whether said mammal has previously encountered said antigen and thus generated MCP-1 reactivity to the antigen
 g) combining the determined IP-10 reactivity and MCP-1 reactivity
thereby determining whether the mammal has previously encountered the antigen and thus generated immunological reactivity to the antigen with at least one biomarker.

In one embodiment, the method comprises,
 a) determining the level of IP-10 in response to the antigenic stimulation,
 b) comparing the level of IP-10 to a reference level or a value derived thereof
 c) determining whether said mammal has previously encountered said antigen and thus generate IP-10 reactivity to the antigen
 d) determining the level of IL-2 in response to the antigenic stimulation,
 e) comparing the level of IL-2 to a reference level or a value derived thereof
 f) determining whether said mammal has previously encountered said antigen and thus generate IL-2 reactivity to the antigen
 g) combining the determined IP-10 reactivity and IL-2 reactivity
thereby determining whether the mammal has previously encountered the antigen and thus generate immunological reactivity to the antigen with at least one biomarker In one embodiment, the method comprises,
 a) determining the level of IP-10 in response to the antigenic stimulation,
 b) comparing the level of IP-10 to a reference level or a value derived thereof
 c) determining whether said mammal has previously encountered said antigen and thus generate IP-10 reactivity to the antigen
 d) determining the level of IFN-γ in response to the antigenic stimulation,
 e) comparing the level of IFN-γ to a reference level or a value derived thereof
 f) determining whether said mammal has previously encountered said antigen and thus generate IFN-γ reactivity to the antigen
 g) combining the determined IP-10 reactivity and IFN-γ reactivity thereby determining whether the mammal has previously encountered the antigen and thus generate immunological reactivity to the antigen with at least one biomarker In one embodiment, the method comprises,
a) determining the level of IP-10 in response to the antigenic stimulation,
b) comparing the level of IP-10 to a reference level or a value derived thereof
c) determining whether said mammal has previously encountered said antigen and thus generate IP-10 reactivity to the antigen
d) determining the level of INF-γ and/or MCP-1 and/or IL-2 in response to the antigenic stimulation,
e) comparing the level of INF-γ and/or MCP-1 and/or IL-2 to reference levels for each biomarker or values derived thereof
f) determining whether said mammal has previously encountered said antigen and thus generate INF-γ and/or MCP-1 and/or IL-2 reactivity to the antigen
d) combining the determined IP-10 reactivity and/or INF-γ and/or MCP-1 and/or IL-2 reactivity thereby determining whether the mammal has previously encountered the antigen and thus generate immunological reactivity to the antigen with at least one of the examined biomarkers Diagnosis In one embodiment, and as stated previously, IP-10 may be used for diagnosis of subjects suspected of various immunological states, such as infections. When used in diagnosis the method according to the present invention may help to determine the presence of immunological states, such as infections, usually accomplished by evaluating clinical symptoms and further laboratory tests. The test may diagnose various stages of infection i.e. a recently encountered infection in an individual without any symptoms, an infection encountered many years back in an individual with no symptoms of that infection, an active infection where the patients has symptoms due to the infection.

In another embodiment IP-10 may be used for diagnosis of subjects suspected of tuberculosis (e.g. active, latent or recent TB infection) and in particular patients at increased risk for progression from latent to active tuberculosis i.e. patients receiving immunosuppressing medication (i.e. monoclonal antibody treatment (anti-CD20 antibodies (e.g. Rituximab©) or TNF-α blocking treatment (e.g. Remicade©, Enbrel©, Humira©))) or steroids or cancer-chemotherapy; or, patients suffering from immunosuppressing conditions (e.g. HIV infection, cancer, IDDM or non-insulin dependent diabetes mellitus (NIDDM), autoimmune conditions, malnutrition, old age, intravenous drug use (IVDU) or inherited immune disorders), and in individuals who have recently been infected. In fact following standard guidelines these patients should be screened for active, latent or recent TB before initiation of medical treatment.

Currently it is strongly recommended to screen patients who are candidates for TNF-α blocker treatment or are HIV positive with either TST or a *M. tuberculosis* antigen-specific IFN-γ test. As studies have shown that these tests may be unreliable in the above mentioned patient categories IP-10 is a better candidate due to its higher sensitivity.

In another embodiment the IP-10 may be used to screen individuals suspected of Chlamydia infection (e.g. uro-genital infection, pelvic infection and/or infection in the eye).

The present invention allows combining antigens from various infectious agents which either colonise the same organ or anatomical region, or generate a common group of symptoms. By combining different specific antigens it may be possible to screen patients at risk, or excluding common pathogens that generate clinical un-distinguishable conditions such as uro-genital infection; or are susceptible to the same treatment e.g. antibiotics.

Thus, in one embodiment the present invention relates to a method for simultaneously screening for at least two infectious diseases comprising
a) obtaining one sample from a patient in need thereof, and dividing said sample in to at least to fractions
b) stimulating one fraction with antigens, wherein said antigens are related to specific infectious agent(s) selected for evaluation (response fraction) incubating the second fraction of the sample with an inactive solution (nil-fraction)
c) measuring the IP-10 level in both fractions
d) determining the antigen-dependent IP-10 level of the sample by subtracting the IP-10 level determined in the nil-fraction from the IP-10 determined from the response fraction
e) comparing said determined antigen-dependent IP-10 level to a reference-level for at least one of the selected infectious agents, and
f) referring said patient in need thereof as infected with at least one of the selected infectious agents if the antigen-dependent IP-10 level is higher than the IP-10 level in the reference fraction.

Accordingly the methods of the present invention may be applicable for screening persons at high risk of infectious diseases e.g. persons who have been staying or travelling through disease endemic areas.

Thus, in an embodiment of the present invention the infectious diseases are selected from the group consisting of malaria, tuberculosis, meningitis, Japanese encephalitis, cholera, leishmanina, dengue and polio.

In another embodiment of the invention the infectious diseases are selected from the sexually transmitted diseases consisting of chancroid, Chlamydia infection, Gonorrhea, Lymphogranuloma venereum, Ureaplasma urealyticum, Mycoplasma hominis, Treponema pallidum, Hepatitis B, Herpes simplex virus, Human Immunodeficiency Virus, Human papillomavirus, Molluscum, Phthirius pubis, Sarcoptes scabiei and Trichomonas vaginalis.

In yet an embodiment of the invention the infectious diseases are selected from the group consisting treatable gastro-intestinal infectious agents e.g. Shigella, *E. Coli, Campylobactor, Vibrio cholerae bacteria, Cryptosporidium parvum, Salmonella bacteri* and *Salmonella typhi bacteria*.

In yet an embodiment of the invention the infectious diseases are selected from the group consisting gastro-intestinal infectious agents not treatable with antibiotics e.g. rotaviruses, noroviruses, adenoviruses, sapoviruses, and astroviruses.

In a further embodiment of the invention the infectious diseases are selected from the group consisting of blood related diseases that are subject to screening e.g. in blood banks: Hepatitis A, Hepatitis E, Malaria, Chagas Disease, Babesiosis, Leishmaniasis, Simian foamy virus, Creutzfelt-Jacob Disease (vCJD), Creutzfeldt-Jakob Disease (CJD), Cytomegalovirus (CMV) and Epstein-Barr Virus.

In one embodiment of the invention the infectious diseases are selected from the group consisting of bacterial able to cause bacterial meningitis, Neisseria meningitides, Streptococcus pneumoniae, Listeria monocytogenes, Pseudomonas aeruginosa, Staphylococcus aureus, Streptococcus agalactiae and Haemophilus influenza.

Accordingly it is object of the present invention to make a species specific diagnosis, because selection of a specific antigen enables the skilled addressee to differentiate between various species of e.g. Mycobacterium.

Prognosis

In one embodiment, IP-10 may be used for predicting the prognosis of subjects diagnosed with various immunological states, such as infections. When used in patient prognosis the method according to the present invention may help to predict the course and probable outcome of the immunological states, such as infections, thus assisting the skilled artisan in selecting the appropriate treatment method and predict the effect of a certain treatment for the condition.

Monitoring

In one embodiment, IP-10 may be used for monitoring subjects diagnosed with infections. When used in patient monitoring the method according to the present invention may help to assess efficacy of treatment during and after termination of treatment e.g. monitoring and predicting possible recurrence of the infection.

The possibility to monitor therapy efficacy by the present invention is particularly relevant because (using infection with *M. tuberculosis* as an example)

a) it is easy to perform by a simple blood draw instead of currently available methods like sputum microscopy, mycobacterium culture, X-ray or other methods b) it is more reproducible compared to sputum microscopy, mycobacterium culture, X-ray or other methods c) it is in-expensive, compared sputum microscopy, mycobacterium culture, X-ray or other methods, invasive surgery procedures involved in a biopsy, e.g. if an extrapulmonary tuberculosis is suspected, or a broncoscopy, if the patient is sputum negative d) it is more sensitive compared to the IFN-γ assays for tuberculosis based on RD1 overlapping peptides;

e) it may distinguish between active and latent tuberculosis while the other immune assays only distinguish infection or no infection.

Screening

In one embodiment, the method according to the present invention is used for screening purposes. I.e., it is used to assess subjects without a prior diagnosis of infections by measuring the level of IP-10 according to the invention and correlating the level measured to a pre-specified level, indicating the presence or absence of various infections (e.g. infection with *M. tuberculosis*). In another embodiment, the method according to the present invention is used for screening purposes. I.e., it is used to assess subjects without a prior diagnosis of infections but at risk of reactivation of latent disease by measuring the level of IP-10 according to a pre-specified level indicating the invention and correlating the level measured to the presence or absence of various infections (e.g. infection with *M. tuberculosis*).

As stated previously the present invention discloses a method for simultaneously screening for at least two infectious diseases.

In another embodiment of the present invention, the method can be used to screen blood from blood-donors for various diseases such as but not limited to infection(s) caused by e.g. parasites or vira.

Contact Tracing

In preferred embodiments, IP-10 may be used for diagnosis of subjects exposed to various infections, such as with *M. Tuberculosis*. When used in contact tracing the method according to the present invention may help to determine the presence of infections, such as infection with *M. tuberculosis*.

In other embodiments, IP-10 may be used for diagnosis of subjects exposed to contagious cases in outbreaks of highly contagious infections, such as, but not limited to Tuberculosis, Corona viruses (e.g. Severe Acquired Respiratory Syndrome), Influenza, Ebola or Marburg virus. In the case of tuberculosis: When used in contact tracing the method according to the present invention may help to determine the presence of infection, usually accomplished by evaluating the TST or the currently available IFN-γ release assay.

Enhanced Case Finding

In preferred embodiments, IP-10 may be used for diagnosis of various diseases, such as infections. When used in enhanced case finding the method according to the present invention may help to determine the presence of infections, such as but not limited to microscopy negative TB which is otherwise difficult to diagnose due to the lack of microbiological evidence of infection but which is usually accomplished by evaluating clinical symptoms, response to treatment, and lack of alternative diagnoses or by time-consuming assays (weeks) such as sputum culture.

Prevalence Studies

In preferred embodiments, IP-10 may be used for studying the prevalence of various immunological states, such as but not limited to infections in populations of interest such as children, HIV positive immigrants, refugees, health care workers, school children, prisoners, laboratory technicians. When used in prevalence studies, the method according to the present invention may help to determine the presence of an infection, such as latent and active TB in a population, usually accomplished by the TST.

Research Purposes

In one embodiment IP-10 may be used by research institutions when screening for potential new antigens derived from a micro organism selected from the group consisting of Mycobacteria, gram positive bacteria, gram negative bacteria, Listeria, enterococci, Neisseria, vibrio, treponema (Syphilis), Borrelia, leptospir, Clamydia, retroviruses (SIV, HIV-1 and HIV-2), corona viruses such as Severe Acute Respiratory Syndrome (SARS) and NL-63, Cytomegalovirus, rotaviruses, metapneumovirus, respiratory syncytium virus (RSV), poxviruses, Ebstein barr virus, enterovirus, morbillivirus, rhabdoviruses (rabies). Rubivirus (rubella), flaviviruses (dengue, yellow fever), herpes viruses, varicellea-zoster virus, Hepatitis C and B, Leishmania, Toxoplasma gondii, trypanosoma, Plasmodium (falciparum, vivax, ovale, malaria), pneumocystis cariini (PCP) and various nematodes, trematodes, these antigens can be e.g. lipids, polysaccharide molecules, proteins and peptides. When used for laboratory research purposes the method according to the present invention may help to determine immune reactivity to the examined antigen, protein or peptide applicable in development of vaccines and diagnostic tests.

Several antigen molecules like for instance peptides are identified as species specific or disease-specific, but their ability to induce T cell reactivity in vivo is difficult to determine due to a lack of sensitive markers. IP-10 determined after stimulation with such candidate antigens can be used to screen for and identify potentially interesting new antigens or molecules. More specifically in the case of antigens derived from *M. tuberculosis, C. trachomatis*, HIV-1 or HCV; IP-10 may be used by research institutions when testing the immunogenicity of these antigens i.e. as a measure of T cell reactivity for the development of e.g. vaccines.

Treatment Effect

The present inventors propose that repeated testing of spontaneous release during incubation (nil sample) and antigen induced IP-10 (Ag sample), during treatment can be used as marker for treatment effect. If spontaneous IP-10 responses decline during treatment, this can be considered successful, whereas, if no decline is observed there a treatment failure must be suspected.

The present inventors propose that repeated testing of spontaneous and antigen induced IP-10 during e.g. TB treatment can be used as marker for treatment effect. If antigen-stimulated IP-10 responses decline during treatment this can be considered successful, whereas if no decline is observed there a treatment failure must be suspected.

It should be understood that any feature and/or aspect discussed herein in connection with the determination according to the invention apply by analogy to the "diagnosis", "prognosis", "monitoring", "screening", "research purposes", "contact tracing", "enhanced case finding" and "prevalence studies" according to the invention and visa versa.

Incubation Step

The cells of the CMI system lose the capacity to mount a CMI response in whole blood after extended periods following blood draw from the subject, and responses without intervention are often severely reduced or absent 24 hours following blood draw, if not treated in a manner that prolongs there life of the cells such as, but not limited to, preservation at a temperature above 10° Celsius.

In one embodiment the reduction of labour allows stimulation of sample with antigens to be performed at the point of care locations such as physicians' offices, clinics, outpatient facilities and veterinary clinics or on farms. Once antigen stimulation is complete, the requirement for fresh and active cells no longer exists. IP-10 and other biomarkers such as cytokines or immune effecter molecules are stable in plasma and, thus, the sample can be stored, frozen or shipped without special conditions or rapid time requirements in a similar fashion to standard plasma samples used for other infectious disease or other disease diagnosis.

The incubation step may be from 5 to 144 hours, more preferably 5 to 120 hours and even more preferably 12 to 24 hours or a time period in between. Thus in one embodiment of the present invention the incubation time is 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 26 hours, 30 hours, 36 hours, 42 hours, 48 hours, 72 hours, 96 hours, 120 hours, or 144 hours.

Because IP-10 is secreted in such high concentrations, it is possible to incubate the samples outside the incubator i.e. on the desk at the laboratory or in a water bath with stable temperature or in a transportable carrying device. This can be especially useful in developing countries or outpatients clinics with basic lab facilities.

The incubation step can take place at a temperature ranging from 20° to 43° Celsius. Thus, in one embodiment of the present invention the incubation temperature may be 16° Celsius, 18° Celsius, 20° Celsius, 22° Celsius, 25° Celsius, 26° Celsius, 27° Celsius, 28° Celsius, 29° Celsius, 30° Celsius, 31° Celsius, 32° Celsius, 33° Celsius, 35° Celsius, 37° Celsius, 38° Celsius, 39° Celsius, 40° Celsius or 41° Celsius.

The incubating step can be performed at a not fixed temperature between, but not limited to, 15° to 40° Celsius, more preferably from 18° to 37° Celsius and even more preferably from 30° to 37° Celsius One embodiment of the invention allows stimulation of sample in dilution to be performed, this with addition of culture media to the cell culture.

Another embodiment of the invention allows stimulation of sample to be performed with addition of inert dilution liquid (e.g. saline) to the cell culture.

Sample

One embodiment of the present invention contemplates a method for measuring a CMI response in a subject, said method comprising collecting a sample from said subject wherein said sample comprises cells of the immune system, which are capable of producing immune effecter-molecules following stimulation by an antigen, incubating said sample with an antigen and then measuring the presence of or elevation in the level of an immune effecter molecule wherein the presence or level of said immune effecter molecule is indicative of the capacity of said subject to mount a cell-mediated immune response.

In one embodiment the sample is derived from the group consisting of blood, urine, pleural fluid, bronchial fluid, oral washings, tissue biopsies, ascites, pus, cerebrospinal fluid, aspitate and follicular fluid.

In a preferred embodiment the sample is derived from blood.

The sample may however also comprise cells selected from the group consisting of whole blood, mononuclear cells from pleural fluid, peripheral blood mononuclear cells (PBMC's), T cells, CD4 T cells, CD8 T cells, gamma-delta T cells, monocytes, macrophages and NK cells.

Conveniently, when the sample is whole blood, the blood collection tube is treated with anticoagulant (e.g. heparin). Notwithstanding that whole blood is the preferred and most convenient sample, the present invention extends to other samples containing immune cells such as but not limited to pleural fluid, ascites fluid, lymph fluid, spinal or cerebral fluid, tissue fluid and respiratory fluid including nasal, and pulmonary fluid.

In one embodiment the present invention thus relates to a method, wherein the sample is derived from blood, urine, pleural fluid, bronchial fluid, oral washings, tissue biopsies, ascites liquid, pus, cerebrospinal fluid, aspitate, and/or follicular fluid.

In another embodiment the present invention thus relates to a method, wherein the sample comprises cells selected from the group consisting of peripheral mononuclear cells, T cells, CD4 T cells, CD8 T cells, gamma-delta T cells, monocytes, macrophages, dendritic cells and NK cells.

In one embodiment, the sample is whole blood, which may be collected in three suitable containers in which, antigen, mitogen or "nil" are present. In another embodiment, antigens, mitogen or "nil" can be added to alliquots containing the sample e.g. whole blood afterwards.

In another embodiment, the sample is whole blood which may be collected in collection tubes containing the antigen, mitogen or "nil" or to aliquots of whole blood to which antigen, mitogen or nil is added.

Generally, blood is maintained in the presence of an anticoagulant (preferably heparin, alternatively e.g. citrate or EDTA). The anticoagulant is present in the blood collection tube when blood is added. The use of blood collection tubes is preferably but not necessarily compatible with standard automated laboratory systems and these are amenable to analysis in large-scale and random access sampling. Blood collection tubes also minimize handling costs and reduce laboratory exposure to whole blood and plasma and, hence, reduce the risk of laboratory personnel from contracting a pathogenic agent such as but not limited to human immunodeficiency virus.

Alliquots of whole blood may be in volumes ranging from 10 μL-4000 μl, such as but not limited to 50 μL, 100 μl, 200 μl, 300 μl, 400 μl, 500 μl, 600 μl, 700 μl, 800 μl, 900 μl, 1000 μl, 1100 μl, 1200 μl, 1300 μl, 1400 μl, 1500 μl, 1600 μl, 1700 μl, 1800 µl, 1900µl, 2000 µl, 2100 µl, 2200 µl, 2300 µl, 2400 µl, 2500 µl, 2600 µl, 2700 µl, 2800 µl, 2900 µl or 3000 µl.

Sample can be incubated in tubes, tissue culture wells or other containers and antigen, mitogen and "nil" can be added in relevant concentrations.

A blood collection-tube includes a vaccutainer-tube or other similar vessel, but blood can also be drawn directly into an open tube or capillary tube.

Kit

The present invention further contemplates a kit for assessing a subject's capacity to mount a cell mediated response. The kit is conveniently in compartmental form with one or more compartments adapted to receive a sample from a subject such as whole blood purified cells, biopsies or other material. That compartment or another compartment may also be adapted to contain heparin where the sample is whole blood.

Generally, the kit is in a form which is packaged for sale with a set of instructions. The instructions would generally be in the form of a method for measuring a CMI response in a subject, said method comprising collecting a sample from said subject wherein said sample comprises cells of the immune system, which are capable of producing immune effecter molecules following stimulation by an antigen, incubating said sample with an antigen supplied with kit and then measuring the presence or elevation in level of IP-10, wherein the presence or level of said immune effecter molecule is indicative of the capacity of said subject to mount a cell-mediated immune response.

In one embodiment the kit contains antigen and monoclonal or polyclonal antibodies, which is specifically reacting with IP-10 in an immune-assay, or specific binding fragments of said antibodies for use as a diagnostic reagent.

The contemplated kit of the present invention may be in a multicomponent form wherein a first component comprises a multiplicity of blood collection tubes, a second component comprises an antibody-based detection means for an immune effecter molecule and a third component comprises a set of instructions which instructions comprise the following: (i) collect blood in the blood collection tubes; (ii) mix the tubes; (iii) incubate the tubes; (iv) centrifuge the tubes and collect the plasma; and (v) detect immune effecter molecules in plasma.

The assay may also be automated or semi-automated and the automated aspects may be controlled by computer software.

The assay of the present invention may be automated or semi-automated for high throughput screening or for screening for a number of immune effecters from the one subject. The automation is conveniently controlled by computer software. The present invention contemplates a computer program product, therefore, for assessing the presence or absence or the level of IP-10, said product comprises (1) code that receives, as input values, the identity of a reporter molecule associated with a labelled antibody or mRNA (2) code that compares said input values with reference values to determine the level of reporter molecules and/or the identity of the molecule to which the reporter molecule is attached; and (3) a computer readable medium that stores the codes.

Still another aspect of the present invention extends to a computer for assessing the presence or absence or level of IP-10, said computer comprises: (1) a machine-readable data storage medium composing a data storage material encoded with machine-readable data, wherein said machine-readable data I comprise input values which identify a reporter molecule associated with a labelled antibody or mRNA;

(2) a working memory for storing instructions for processing said machine-readable data;

(3) a central-processing unit coupled to said working memory and to said machine readable data storage medium, for processing said machine readable data to compare said values to provide an assessment of the identity or level of reporter molecules or of molecules to which they are attached; and (4) an output hardware coupled to said central processing unit, for receiving the results of the comparison.

Specificity and Sensitivity

The sensitivity of any given diagnostic test define the proportion of individuals with a positive response who are correctly identified or diagnosed by the test, e.g. the sensitivity is 100%, if all individuals with a given condition have a positive test. The specificity of a given screening test reflects the proportion of individuals without the condition who are correctly identified or diagnosed by the test, e.g. 100% specificity is, if all individuals without the condition have a negative test result.

Sensitivity is defined as the proportion of individuals with a given condition (e.g. active TB infection), who are correctly identified by the described methods of the invention (e.g. has a positive IP-10 test result).

Specificity herein is defined as the proportion of individuals without the condition (e.g. active TB infection), who are correctly identified by the described methods of the invention (e.g. has a negative IP-10 test result)

Receiver-Operating Characteristics

Accuracy of a diagnostic test is best described by its receiver-operating characteristics (ROC) (see especially Zweig, M. H., and Campbell, G., Clin. Chem. 39 (1993) 561-577). The ROC graph is a plot of all of the sensitivity/specificity pairs resulting from continuously varying the decision threshold over the entire range of data observed.

The clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example health and disease, latent or recent infection versus no infection, or benign versus malignant disease.

In each case, the ROC plot depicts the overlap between the two distributions by plotting the sensitivity versus 1—specificity for the complete range of decision thresholds. On the y-axis is sensitivity, or the true-positive fraction [defined as (number of true-positive test results) (number of true-positive+number of false-negative test results]. This has also been referred to as positivity in the presence of a disease or condition. It is calculated solely from the affected subgroup. On the x axis is the false-positive fraction, or 1—specificity [defined as (number of false-positive results)/(number of true-negative+number of false-positive results)]. It is an index of specificity and is calculated entirely from the unaffected subgroup.

Because the true-and false-positive fractions are calculated entirely separately, by using the test results from two different subgroups, the ROC plot is independent of the prevalence of disease in the sample. Each point on the ROC plot represents a sensitivity/—specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. (If the ROC plot falls completely below the 45° diagonal, this is easily remedied by reversing the criterion for "positivity" from "greater than" to "less than" or vice versa.) Qualitatively, the closer the plot is to the upper left corner, the higher the overall accuracy of the test.

One convenient goal to quantify the diagnostic accuracy of a laboratory test is to express its performance by a single number. The most common global measure is the area under the ROC plot. By convention, this area is always $\geq 0.5$ (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

Clinical utility of the novel marker IP-10 may be assessed in comparison to and in combination with other diagnostic tools for the given infection. In the case of infection with *M. tuberculosis* clinical utility of the novel marker IP-10 may be assessed in comparison to established diagnostic tools established marker IFN-γ or the TST using a receiver operator curve analysis. See examples 5.

Thus, it is an object of preferred embodiments of the present invention to provide an immunological method for detecting whether a mammal has encountered an antigen, the method comprising:
  a) determining the level of antigen-specific IP-10 production in a sample of said mammal
  b) constructing a percentile plot of the IP-10 level obtained from a healthy population
  c) constructing a ROC (receiver operating characteristics) curve based on the IP-10 level determined in the healthy population and on the IP-10 level determined in a population who has generated immunological reactivity to the antigen in question
  d) selecting a desired specificity
  e) determining from the ROC curve the sensitivity corresponding to the desired specificity
  f) determining from the percentile plot the IP-10 level corresponding to the determined sensitivity; and
  g) predicting the individual to have immunological reactivity to the antigen, if the level of IP-10 in the sample is equal to or higher than said IP-10 level corresponding to the determined specificity and predicting the individual as unlikely or not to having immunological reactivity to the antigen if the level of IP-10 in the sample is lower than said total IP-10 level corresponding to the determined specificity.

Thus, it is another object of preferred embodiments of the present invention to provide an immunological method for detecting whether a mammal has encountered an antigen, the method comprising:
  a) determining the level of antigen-specific IP-10 production in a sample of said mammal
  b) constructing a percentile plot of the IP-10 level obtained from a healthy population
  c) constructing a ROC (receiver operating characteristics) curve based on the IP-10 level determined in the healthy population and on the IP-10 level determined in a population who has generated immunological reactivity to the antigen in question
  d) selecting a desired sensitivity
  e) determining from the ROC curve the specificity corresponding to the desired sensitivity
  f) determining from the percentile plot the IP-10 level corresponding to the determined sensitivity; and
  g) predicting the individual to have immunological reactivity to the antigen if the level of IP-10 in the sample is equal to or higher than said IP-10 level corresponding to the determined sensitivity and predicting the individual as unlikely or not to having immunological reactivity to the antigen if the level of IP-10 in the sample is lower than said total IP-10 level corresponding to the determined sensitivity.

The specificity of the method according to the present invention may be from 70% to 100%, more preferably 80% to 100%, more preferably 90% to 100%. Thus in one embodiment of the present invention the specificity of the invention is 80%, 81%, 82%, 83%, 84%, 85%, 86%, 87%, 88%, 89%, 90%, 91%, 92%, 93%, 94%, 95%, 96%, 97%, 98%, 99% or 100%.

The sensitivity of the method according to the present invention may be from 70% to 100%, more preferably 80% to 100%, more preferably 90% to 100%. Thus in one embodiment of the present invention the sensitivity of the invention is 80%, 81%, 82%, 83%, 84%, 85%, 86%, 87%, 88%, 89%, 90%, 91%, 92%, 93%, 94%, 95%, 96%, 97%, 98%, 99% or 100%. See example 5.

The level of IP-10 is compared to a set of reference data or a reference value such as the cut-off value to determine whether the subject is at an increased risk or likelihood of e.g. infection.

To increase detection efficiency the blood level of IP-10 may be compared to a set of reference data to determine whether the subject is likely to be infected or is at increased risk of developing of e.g. infection.

To increase detection efficiency, PHA induced IP-10 level and the antigen stimulated level of IP-10 may be compared to a set of reference data to determine whether the subject has the infection or is at increased risk of developing infection or disease.

To determine whether the patient is at increased risk of developing e.g. infection, a cut-off must be established. This cut-off may be established by the laboratory, the physician or on a case by case basis by each patient.

Alternatively cut point can be determined as the mean, median or geometric mean of the negative control group ((e.g. not infected, healthy unexposed, patients without TB infection)+/− one or more standard deviations or a value derived from the standard deviation)

Following antigen challenge some individuals respond strongly to biomarker while not to another. For instance some individuals may not show either IP-10 or IFN-γ responses, thus only producing low levels of IP10 or IFN-γ. In these cases simultaneous measurement of two, three, four or more biomarkers will increase sensitivity of the assay and increase the number of positive responders. By combining IP-10 and one or more biomarkers such as but not limited to IFN-γ, IL-2, or MCP-1, it is therefore possible to make diagnostic predictions that are less vulnerable to single biomarker anergy.

In another preferred embodiment, IP-10 measurements are combined with measurements of one or more other biomarkers, and compared to a combined reference-level. The measured biomarker levels can be combined by arithmetic operations such as addition, subtraction, multiplication and arithmetic manipulations of percentages, square root, exponentiation, and logarithmic functions. Various biomarker combinations and various means of calculating the combined reference-value can be performed by means known to the skilled addressee.

In another preferred embodiment individual measurements of biomarkers (such as but not limited to IP-10 in combination with IFN-γ and/or IL-2) can be combined after the individual biomarker concentration is compared to a reference-level, e.g. a cut-off point. This approach generates a test result covering not only several antigens but also several biomarkers in one. Various biomarker combinations and various means of calculating the combined reference-value can be performed by means known to the skilled addressee.

In one embodiment of the present invention the combination of the biomarker IP-10 and one of the biomarkers selected from the group consisting of MCP-1, IL-2 and INF-γ provides a synergistic effect in relation to sensitivity and/or specificity.

In yet another embodiment of the present invention the combination of the biomarker IP-10, MCP-1 and IL-2 provides a synergistic effect in relation to sensitivity and/or specificity.

In a further embodiment of the present invention the combination of the biomarker IP-10, MCP-1 and IFN-γ provides a synergistic effect in relation to sensitivity and/or specificity.

In another embodiment of the present invention the combination of the biomarker IP-10, IL-2 and IFN-γ provides a synergistic effect in relation to sensitivity and/or specificity.

Specifically as used herein synergy refers to the phenomenon in which several biomarkers acting together creates a "combined biomarker signal" with greater sensitivity or specificity for diagnosis, than that predicted by knowing only the separate biomarkers sensitivity or specificity, thus reduce the number of false positive and increase the discriminatory power.

In an antibody based readout such as but not limited to the ELISA or immunocromatographic stick test; two or more antibodies binding different biomarkers will enable an increased binding of the total amount of biomarker, hereby acting in synergy and leading to stronger responses and increased sensitivity in the test. A combined readout can be performed in accordance with the teachings herein.

Risk Assessment

The present inventors have successfully identified a new marker for measuring a cell-mediated response to an antigen. The concentration of the marker IP-10 is increased in subjects with a cell mediated immune-response to an antigen. And IP-10 appears to be an efficient marker for detection of e.g. infection with *M. tuberculosis*.

The sensitivity is higher than any other established marker and the specificity is comparable or better than with any other established marker, see e.g. example 4, 5 and 10).

Statistical reasoning can for example be based on the risk of having the disease depending on age, occupation, exposure, genetic background, HLA-type.

Cut-off points can vary based on specific conditions of the individual tested such as but not limited to the risk of having the disease, occupation, geographic residence or exposure.

Cut-off points can vary based on specific conditions of the individual tested such as but not limited to age, sex, genetic background (i.e. HLA-type), acquired or inherited compromised immune function (e.g. HIV infection, diabetes, patients with renal or liver failure, patients in treatment with immune-modifying drugs such as but not limited to corticosteroids, chemotherapy, TNF-α blockers, mitosis inhibitors).

Doing adjustment of decision or cut-off limit will thus determine the test sensitivity for detecting an infection, if present, or its specificity for excluding infection or disease if below this limit. Then the principle is that a value above the cut-off point indicates an increased risk and a value below the cut-off point indicates a reduced risk.

In addition test samples with indeterminate results must be interpreted separately. Indeterminate results are defined as result with an unexpectedly low level of IP-10 in the mitogen stimulated sample (PHA). The final cut point for an indeterminate IP-10 result may be decided according to the study group, especially in immunosuppressed the cut-off level may be selected at a lower level.

Cut-Off Levels

As will be generally understood by those of skill in the art, methods for screening for cell-mediated immune reactivity are processes of decision making by comparison. For any decision-making process, reference-values based on subjects having the disease or condition of interest and/or subjects not having the disease, infection, or condition of interest are needed.

The cut-off level (or the cut-off point) can be based on several criteria including the number of subjects who would go on for further invasive diagnostic testing, the average risk of having and/or developing e.g. infection to all the subjects who go on for further diagnostic testing, a decision that any subject whose patient specific risk is greater than a certain risk level such as e.g. 1 in 400 or 1:250 (as defined by the screening organization or the individual subject) should go on for further invasive diagnostic testing or other criteria known to those skilled in the art.

The cut-off level can be adjusted based on several criteria such as but not restricted to certain group of individuals tested. E.g. the cut-off level could be set lower in individuals with immunodeficiency and in patients at great risk of progressing to active disease, cut-off may be higher in groups of otherwise healthy individuals with low risk of developing active disease.

In one embodiment the present invention discloses a method for determining if a subject has an infection, which comprises:
  (a) obtaining from the subject a sample, and
  (b) quantitatively determining the concentration of IP-10 present in the sample, the presence of the IP-10 polypeptide present in the sample at a concentration equal to or higher than the selected cut-off indicating that the subject is likely to have infection.

More specifically one aspect of the present invention relates to an immunological method comprising the steps of
  a) incubating a sample obtained from a mammal with at least one antigen
  b) determining the IP-10 level in said sample
  c) comparing said determined IP-10 level with a reference-level, thereby determining whether mammal has previously encountered the antigen generating immunological reactivity to the antigen or previously encountered other antigens generating immunological cross reactivity to the antigen.

More specifically another aspect of the present invention relates to an immunological method comprising the steps of
  a) incubating a sample obtained from a mammal with at least one antigen without any subsequent stimulation and with the proviso that the antigen is not PPD,
  b) determining the IP-10 level in said sample
  c) comparing the determined IP-10 level with a reference-level, thereby determining whether said mammal has previously encountered said at least one antigen generating immunological reactivity to said antigen(s) or previously encountered other antigens generating immunological cross reactivity to the antigen(s).

In one embodiment, the present invention relates to a method according to the present invention, wherein the sample is divided into at least 2 fractions and
  a) incubating a sample obtained from a mammal with at least one antigen without any subsequent stimulation and with the proviso that the antigen is not PPD to generate a response sample
  b) incubating the second fraction of the sample with an inactive solution to generate a nil sample
  c) determining the IP-10 level in the two fractions
  d) determining the antigen-dependent IP-10 response of the sample by subtracting the IP-10 level determined in the nil sample from the IP-10 determined in the response sample
  e) comparing the antigen-dependent IP-10 response or a value derived thereof with the reference-level or a value derived thereof, thereby determining whether mammal has previously encountered the antigen and thus generate immunological reactivity to the antigen or previously encountered other antigens generating immunological cross reactivity to the antigen and/or is going to develop infection.

The discriminating value is a value which has been determined by measuring the parameter or parameters in both a healthy control population and a population with known infection thereby determining the discriminating value which identifies the infected population with either a predetermined specificity or a predetermined sensitivity based on an analysis of the relation between the parameter values and the known clinical data of the healthy control population and the infection patient population, such as it is apparent from the detailed discussion in the examples herein. The discriminating value determined in this manner is valid for the same experimental setup in future individual tests.

In the specific experimental setups described herein (example 5), the level threshold of IP-10 useful as a cut-off value was found to be in the range of but not limited to 14 pg/ml to 1000 pg/ml. Preferably the cut-off is in the range between 100 pg/ml and 800 pg/ml such as in the range of 100-600 e.g. in the range of 150-400, such as in the range of 150-300, e.g. in the range of 150-250, such as in the range of 175-215.

Preferably the cut-off value is 180 pg/ml, 181 pg/ml, 182 pg/ml, 183 pg/ml, 184 pg/ml, 185 pg/ml, 186 pg/ml, 187 pg/ml, 188 pg/ml, 189 pg/ml, 190 pg/ml, 191 pg/ml, 192 pg/ml, 193 pg/ml, 194 pg/ml, 195 pg/ml, 196 pg/ml, 197 pg/ml, 198 pg/ml, 199 pg/ml, 200 pg/ml, 201 pg/ml, 202 pg/ml, 203 pg/ml, 204 pg/ml, 205 pg/ml, 206 pg/ml, 207 pg/ml, 208 pg/ml, 209 pg/ml, 210 pg/ml, 211 pg/ml, 212 pg/ml, 213 pg/ml, 214 pg/ml, 215 pg/ml, 216 pg/ml, 217 pg/ml, 218 pg/ml, 219 pg/ml, 220 pg/ml, 221 pg/ml, 222 pg/ml, 223 pg/ml, 224 pg/ml or 225 pg/ml.

Dilution of sample, combined measurements with other parameters such as but not limited to interleukin-2, interferon gamma and/or macrophage chemotactic protein-1, or other parameters will result in other cut-off values, which can be determined in accordance with the teachings herein. Other experimental setups, other samples, other antigens, and other parameters will of course result in other cut-off values, which can be determined in accordance with the teachings herein by a person skilled in the art by normal design procedures or routine experiments.

The level of induced antigen specific biomarker level is also depending on the antigens chosen for stimulation. Some antigens are more potent inducers than others, but also the number of different available antigens i.e. peptides will result in increased number of responding cells and higher biomarker production. Therefore a cut-off point is also antigen-dependent, and disease dependent. Furthermore other species have other major histocompatability antigen repertoires therefore the same antigens tested in different species will result in species-specific cut-offs.

Measurements of biomarker concentration can be translated to international units (IU). IU relates to the biological activity of the biomarker and is a reference to benchmark between various methods of measurements.

In other embodiments of the invention the determined cut-off value can be combined with a stimulation-index (defined as antigen-stimulated IP-10 concentration divided by the un-stimulated plasma concentration).

A stimulation-index value was found to be in the range of but not limited to 1 to 6 or above. Preferably, the stimulation-index is at least 1.25, 1.5, 1.75, 2, 2.25, 2.5, 2.75, 3, 3.25, 3.5, 3.75, or 4. The present invention even discloses stimulation-index value in the range of several hundreds folds. Thus, stimulation-index value of at least 10, 20, 50, 75, 100, 200, 300, or even 1000 is contemplated.

Cut-off and stimulation-index can be different for latent infection, recent infection, sub-clinical infection or active infection. More specifically in the case of infection with *M. tuberculosis* the cut-off value and stimulation-index can be different for e.g. extra pulmonary TB, pulmonary TB, or both, cured infection, latent TB. Cut-off and stimulation-index, level of variation can be different where infection is found in the presence of HIV, other co-infections, immune suppression.

Depending on the prevalence or expected prevalence of presence of disease, the cut-off level and/or the stimulation-index can be adjusted for obtaining as few false positive or as few false negative results as wanted, depending on the severity of the disease and the consequences of determining, whether the patient is positive for the test or negative for the test. In the case of tuberculosis the assay presented in this invention has a clear advantage to the other in vitro tests presently available. Because the antigen-specific IP-10 production is higher than the produced IFN-γ (see e.g. example 4 and 17), the cut-off and stimulation-index can be adjusted in broader ranges, thus widening the opportunity for diagnosis.

The cut-off level can be different, if a single patient with symptoms has to be diagnosed or the test is to be used in a screening of a large number of individuals in a population.

The cut-off and stimulation-index can be based on combined IP-10 measurements and measurements of other biomarkers such as but not limited to Interleukin-2, interferon gamma (INF-γ) and/or monocyte/macrophage chemotactic protein 1 (MCP-1). A compound cut-off and/or stimulation-index may result in other values, which can be determined in accordance with the teachings of the present invention.

Although any of the known analytical methods for measuring the levels of these analytes will function in the present invention, as obvious to one skilled in the art, the analytical method used for each marker must be the same method used to generate the reference data for the particular marker. If a new analytical method is used for a particular marker or combination of markers, a new set of reference data, based on data developed with the method, must be generated.

The multivariate DISCRIMINANT analysis and other risk assessments can be performed on the commercially available computer program statistical package Statistical Analysis System (manufactured and sold by SAS Institute Inc.) or by other methods of multivariate statistical analysis or other statistical software packages or screening software known to those skilled in the art.

As obvious to one skilled in the art, in any of the embodiments discussed above, changing the risk cut-off level of a positive test or using different a priori risks which may apply to different subgroups in the population, could change the results of the discriminant analysis for each patient.

The stability tests described herein propose that IP-10 is highly stable with routine handling (i.e. freezing or storage for prolonged periods of time at room temperature and temperatures below 10 C); thus, the present inventors conclude that IP-10 is an attractive analyte for clinical use. The data presented here suggest that IP-10 is a potentially valuable marker for use in prognosis, diagnosis, monitoring and screening of infectious diseases.

In order to determine the clinical severity of cell-mediated immune reactivity, means for evaluating the detectable signal of IP-10 measured involves a reference or reference means.

The reference also makes it possible to count in assay and method variations, kit variations, handling variations, variations related to combining IP-10 and other biomarkers, and other variations not related directly or indirectly to the IP-10 level.

In the context of the present invention, the term "reference" relates to a standard in relation to quantity, quality or type, against which other values or characteristics can be compared, such as e.g. a standard curve.

The reference data reflect the level of IP-10 for subjects having cell-mediated immune reactivity (also referred to as affected, exposed, vaccinated, infected or diseased) and/or the level of IP-10 for normal subjects (also referred to as unaffected, unexposed, un vaccinated, uninfected, or healthy).

In yet an embodiment of the present invention, the device is selected from the group consisting of an assay, an immunoassay, a stick, a dry-stick, an electrical device, an electrode, a reader (spectrophotometric readers, IR-readers, isotopic readers and similar readers), histochemistry, and similar means incorporating a reference, filter paper, colour reaction visible by the naked eye.

IP-10

IFN-γ-inducible protein 10 (IP-10) or CXCL10 is a chemokine. The IP-10 gene is mapped to 4q21 by in situ hybridization. IP-10 expression is up regulated by Interferons (IFNs i.e. Interferon gamma (IFN-γ)) and inflammatory stimuli, and it is expressed in many Th1-type inflammatory diseases in a variety of tissues and cell types.

The human gene sequence can be found under ACCESSION number BC010954 (gi 15012099) in Gene Bank.

Chemokines are a group of small (approximately 8 to 14 kD), mostly basic, structurally related molecules that regulate cell trafficking of various types of leukocytes through interactions with a subset of 7-transmembrane, G protein-coupled receptors. Chemokines also play fundamental roles in the development, homeostasis, and function of the immune system, and they have effects on cells of the central nervous system as well as on endothelial cells involved in angiogenesis or angiostasis. Chemokines are divided into 2 major subfamilies, CXC and CC, based on the arrangement of the first 2 of the 4 conserved cysteine residues; the 2 cysteines are separated by a single amino acid in CXC chemokines and are adjacent in CC chemokines. CXC chemokines are further subdivided into ELR and non-ELR types based on the presence or absence of a glu-leu-arg sequence adjacent and N terminal to the CXC motif. ELR types are chemotactic for neutrophils, while non-ELR types are chemotactic for lymphocytes.

IP-10 inhibits bone marrow colony formation, has antitumor activity in vivo, is a chemoattractant for human monocytes and T cells, and promotes T cell adhesion to endothelial cells. IP-10 is a potent inhibitor of angiogenesis in vivo. IP-10 may participate in the regulation of angiogenesis during inflammation and tumorigenesis. IP-10 is also a RAS target gene and is overexpressed in the majority of colorectal cancers. Using nuclear magnetic resonance spectroscopy it has been showed that IP-10 interacted with the N terminus of CXCR3 via a hydrophobic cleft formed by the N-loop and 40s-loop region of IP-10, similar to the interaction surface of other chemokines, such as IL8. An additional region of interaction was found that consisted of a hydrophobic cleft formed by the N terminus and the 30s loop of IP-10. Suggesting that a mechanism involving the 30s loop and the configuration of beta strand 2 may account for the interaction and antagonistic function of IP-10 with CCR3.

In the case of tuberculosis high levels of IP-10 have been found in lymph node and lung tuberculous granulomas, in pleural effusions and in the serum or plasma of TB patients and TB-HIV co-infected experiencing immune reconstitution syndrome.

IP-10 Level Determination

The immune effecter molecule is preferably a cytokine such as but not limited to IP-10. The presence or level of immune effecter may be determined at the level of the molecule itself or to the extent to which a gene is expressed. The level of IP-10 is measured by conventional analytical methods, such as immunological methods known to the art.

Measurements of the immune-effector can be combined with measurements of other immune effectors at gene, RNA, or protein level in accordance with the teachings herein.

As stated above, detection of the immune effector molecules may be made at the protein or nucleic acid levels. Consequently, reference to presence or level of said immune effector molecule includes direct and indirect data. For example, high levels of IP-10 mRNA are indirect data showing increased levels of IP-10. Ligands to the immune effecters are particularly useful in detecting and/or quantitating these molecules.

Antibodies to the immune effecters are particularly useful. Techniques for the assays contemplated herein are known in the art and include, for example, sandwich assays, xMAP multiplexing, Luminex, ELISA and ELISpot. Reference to antibodies includes parts of antibodies, mammalianized (e.g. humanized) antibodies, recombinant or synthetic antibodies and hybrid and single chain antibodies.

Both polyclonal and monoclonal antibodies are obtainable by immunization with the immune effecters or antigenic fragments thereof and either type is utilizable for immunoassays. The methods of obtaining both types of sera are well known in the art.

Polyclonal sera are less preferred but are relatively easily prepared by injection of a suitable laboratory animal with an effective amount of the immune effecter, or antigenic part thereof, collecting serum or plasma from the animal and isolating specific sera by any of the known immuno-adsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Detection can also be obtained by either direct measure of IP-10 using specific antibody in a competitive fluorescent polarization immunoassay (CFIPA) or by detection of homodimerization of interferon-gamma by dimerization induced fluorescence polarization (DIFP). In either case, detection and quantitation will be down to or less than 6 pg/ml.

With the method presently used in the supplied example material the detection limit of the assay is 6 pg/ml, with modifications this may be lower.

If sample material is diluted IP-10 concentration in said sample will be lower but still determinable (see example 9). Other experimental setups and other parameters will result in other values, which can be determined in accordance with the teachings herein.

Several techniques are known to the skilled addressee for determination of biological markers such as IP-10. The presence or level of immune effecter may be determined by ELISA, Luminex, ELISPOT, mRNA based techniques like RT-PCR or Intracellular flow cytometri.

Luminex

Interferon gamma (IFN-γ) has been the gold standard for Th1 response in infectious diseases immunology and especially in TB immunology. IFN-γ determined by Luminex is a poor marker because of lower sensitivity compared to the commercial ELISA developed for the Quantiferon test (See Example 10). IP-10 however is easily detected by Luminex and may therefore replace IFN-γ as a research or screening tool in the Luminex system.

The data provided for in some of the examples below are generated by the use of Luminex, which allows multiplexing of analytes in solution with flow cytometry. Using a propriety technique, Luminex internally color codes xMAP microspheres by combining different ratios of two fluorescent dyes. Each bead set is conjugated with a different capture antibody. The use of R-phycoerythrin-labeled detection antibodies allows quantification of antigen-antibody reactions occurring on the microsphere surface, by measurement of the relative fluorescence intensity.

The system is capable of measuring many samples in small volumes, and up to 100 different analytes can be measured simultaneously in a single 50 µl sample.

The current data was obtained according to the Biosource protocol. Briefly, bead suspensions from individual IP-10, and IFN-γ kits were combined in pre-wetted filter 96 plate wells. The beads were washed twice with wash solution and incubation buffer was added.

Samples (here 4-50 µl) were diluted 1:32, 1:10, 1:8 or 1:1 in assay dilution and added to the plate. The plate was incubated 2 hours at room temperature at 600 rpm on a titer plate shaker. After two washes, 100 µl detection antibody cocktail was added per well, and the plate was incubated at room temperature for one hour on a titer plate shaker. After two washes, 100 µl of strepavidin-RPE solution was added per well. Finally, after 30 minutes incubation and three washes, 100 µL of wash solution was added to each well and the plate was placed in the XY platform of the Luminex.

From each well, a minimum of 100 analyte specific beads were analyzed for both bead- and RPE fluorescence.

ELISA

The data provided for in some of the examples below are generated by the use of ELISA according to the Biosource protocol. Samples (5 µL to 50 µL) were added to the wells of a 96 flat bottomed plate preloaded with IP-10 antibodies. 50 µL of Biotin Conjugate was added to all wells. The plate was covered and incubated at room temperature for 3 hours before the contents of the wells were aspirated and washed 4× with Working Wash Buffer. Then 100 µL of diluted Streptavidin-HRP was added to all wells and the plate was covered and incubated at room temperature for 30 minutes. Then the wells were aspirated and washed 4× with Working Wash Buffer before 50 µL of Stabilized Chromogen was added to each well and the plate incubated at room temperature for 30 minutes, protected from light. Finally 100 µL of Stop Solution was added to each well and the plate was read on an ELISA reader at 450 nm. Immunochromatographic tests (ICT).

Immunochromatographic Tests (ICT)

Test Principle: ICT (e.g. a lateral stick) is an in vitro immunodiagnostic test that utilizes a primary antibody (Ab) and one to four secondary Ab's all specific for IP-10. The primary Ab is attached to colloidal gold and impregnated into a sample pad with a lane containing one secondary Ab in a fixed line.

In the first step the incubated sample is added to the left part of the sample pad. Serum or plasma will flow forward into the lane allowing any IP-10 present to bind to the colloidal gold-labeled primary Ab. The secondary Ab is immobilized in a line across the membrane of the lane. When the card is closed, the sample and the labelled primary Ab on the lane of the pad contact the end of the membrane. The sample and the labelled primary Ab then migrate along the membrane lane crossing the immobilized secondary Ab line. Test interpretation: Any IP-10 complexed with the gold-labelled primary Ab is captured by the secondary Ab on the membrane and a colour change occurs in the line. Test is then interpreted either a. on the basis of the colour intensity or b. by comparing two tests, one performed on the response sample (e.g. plasma of antigen stimulated test material like whole blood) and one performed on the nil sample, one subtracts the intensity of the colour change in the nil test from the intensity of the colour change in the Ag test and compare this is to a reference.

The readout of the test may also be automated or semi-automated using a computerized interface. This setup could be constructed so the automated interface determines an intensity of the colour change of the line.

Infection

One aspect of the present invention relates to a method, wherein the antigen-specific IP-10 response above the reference-level indicate that the mammal has previously encountered the antigen or previously encountered other antigens generating cross reactivity to the antigen because of e.g an infectious stage such as active disease, active subclinical infection, recent or latent infection or vaccinated).

Micro Organism

According to the present invention the infections may be cause by a micro organims, such as but not limited to bacteria, parasites, fungi, viruses, prions, and/or viroids In a presently preferred embodiment the micro organism is selected from the group consisting of Mycobactiera, gram positive bacteria, gram negative bacteria, Listeria, enterococci, Neisseria, vibrio, treponema (Syphilis), Borrelia, leptospirae, Clamydia, retroviruses (SIV, HIV-1, HIV-2), Cytomegalovirus, poxviruses, Ebstein barr virus, enterovirus, morbillivirus, rhabdoviruses (rabies). Rubivirus (rubella), flaviviruses (dengue, yellow fever), herpes viruses, varicella-zoster virus, Hepatitis C and B, Leishmania, Toxoplasma gondii, trypanosoma, Plasmodium (falciparum, vivax, ovale, malaria), pneumocystis cariini (PCP), Coronavirus (e.g. Severe Acquired Respiratory Syndrome (SARS)), Ebola or Marburg and various nematodes, trematodes.

In an even more preferred embodiment the micro organism is selected from the group consisting of Mycobactiera, Leishmaniasis, Clamydia, Tryphanosomasis and Schistosomiasis.

In the case wherein the infection is or were caused by Mycobacteria, said Mycobacteria belongs to the *M. tubercu-* losis complex organisms (*M. tuberculosis, M. bovis* and *M. africanum*), Mycobacteria where the region of difference (RD1) has not been deleted (*M. kansasii, M. szulgai, M. marinum, M. flavescens, M. gastrii*), Mycobacteria pathogenic to humans (*M. avium* and *M. lepra*) and other non-tuberculous mycobacteria.

Thus, in one presently preferred embodiment the Mycobacteria is *M. tuberculosis*.

In the case wherein the infection is or was caused by Chlamydia, said Chlamydia may be selected from the group consisting of *C. trachomatis, C. muridarum*, and *C. suis, C. pneumoniae* and or *C. psittaci*.

In a preferred embodiment of the present invention the Chlamydia is C. trachomatis.

Vaccination

One aspect of the present invention relates to a method, wherein the antigen-dependent IP-10 response above the reference-level indicate that the mammal has previously encountered the antigen or previously encountered other antigens generating cross reactivity to the antigen because of a vaccination against any micro-organism mentioned herein.

Response to a vaccine based on non-viable material may result in low levels of antigen-specific IFN-γ release and because IP-10 is released in high amounts it may be used to detect vaccine responses in preclinical, clinical trials, and subsequently in a routine setting.

Tuberculosis

Tuberculosis (commonly abbreviated as TB) is an infectious disease caused by the bacterium Mycobacterium tuberculosis, which most commonly affects the lungs (pulmonary TB) but can also affect all other organs in the body e.g. the central nervous system (meningitis), lymphatic system, circulatory system (miliary tuberculosis), genitourinary system, bones and joints. Infection with *M. tuberculosis* can also remain asymptomatic a stage which is commonly known as latent, dormant or sub-clinical TB infection.

In a presently preferred embodiment, the present invention relates to a method of diagnosing and monitoring various e.g. distinct presentations of tuberculosis: active tuberculosis disease, active microscopy positive or microscopy negative TB infection, latent tuberculosis infection, and recent tuberculosis infection.

The immune assay is based on the evaluation of the production of IP-10 by antigen-specific T lymphocyte in interaction with antigen presenting cells (e.g. monocytes/macrophages) responding to selected peptide sequences of secretory proteins of MTB. These peptide sequences have been selected for their immunogenicity and their specificity, and potentially other peptides can be used similarly.

The method and the kit can be used for diagnosing active tuberculosis disease, for diagnosing a recent infection in healthy contacts of a patient with a sputum-positive pulmonary tuberculosis, for diagnosing healthy with latent infection, for monitoring the response to treatment in the case of pulmonary and extra-pulmonary tuberculosis and to discriminate between latent infection and active tuberculosis disease state Chlamydia Chlamydia is a common term for infection with any bacterium belonging to the phylum Chlamydiae. *Chlamydia trachomatis* is a major infectious cause of human eye and genital disease. *C. trachomatis* is naturally found living only inside human cells and is one of the most common sexually transmitted infections in people worldwide—about four million cases of chlamydia infection occur in the United States each year. Not all infected people exhibit symptoms of infection. About half of all men and three-quarters of all women who have chlamydia have no symptoms and do not know that they are infected. It can be serious but is easily cured with antibiotics if detected in time. Equally important, chlamydia infection of the eye is the most common cause of preventable blindness in the world.

In a presently preferred embodiment, the present invention relates to a method of diagnosing and monitoring Chlamydia infection.

The immune assay is based on the evaluation of the production of IP-10 by antigen-specific T lymphocyte in interaction with antigen presenting cells (e.g. monocytes/macrophages) responding to crude antigens or purified antigens such as but not limited to peptides. Potentially peptide sequences could be selected for their immunogenicity and their specificity, and potentially other peptides can be used similarly.

Antigen

The choice of antigen suitable for the present invention, also referred to as test-antigen(s) and antigen selected for evaluation, depends on the type of infection the skilled addressee would like to assess, accordingly the selected antigens are disease associated. For example when monitoring MTB infection any available MTB antigens could generate the necessary response and vice versa. Several antigens are already used in the existing commercial assays. It should be understood that any feature and/or aspect discussed above or below in connection with the test-antigen(s) according to the invention apply by analogy to the antigen selected for evaluation.

Wherein the infection is believed to be related to tuberculosis, the antigen or the at least one antigen is selected from the group consisting of RD-1 antigens, ESAT-6, CFP10, TB7.7, Ag 85, HSP-65, Ag85A, Ag85B, MPT51, MPT64, TB10.4, Mtb8.4, hspX, Mtb12, Mtb9.9, Mtb32A, PstS-1, PstS-2, PstS-3, MPT63, Mtb39, Mtb41, MPT83, 71-kDa, PPE68 and LppX.

In a presently preferred embodiment the antigen or the at least one antigen is selected from the group consisting of ESAT-6, CFP-10 TB 7.7, Ag 85,HSP 65 and RD-1 antigens.

In yet an embodiment of the present invention the antigen is ESAT-6.

In another embodiment of the present invention the antigen is CFP-10.

In a further embodiment of the present invention the antigen is TB 7.7.

In a presently preferred embodiment of the present invention the antigens are RD-1 antigens.

Several research institutions are working on identification of antigens solemnly expressed by the individual infectious agent, so called microbe- or disease-specific antigens. In the case of *M. tuberculosis*, specific antigens are expressed at different stages of infection such as but not limited to dormant, latent, active, recent, pulmonary, extrapulmonary, localized or cured stages.

The present invention can be implemented using such antigens thus providing a tool for identification of that specific stage (e.g. latent infection with *M. tuberculosis*).

In a preferred embodiment, several antigens from the same micro organism can be added when generating the response sample. By adding several antigens with various tissue type preferences the strength of the assay is increased. In the case of tuberculosis, combining antigen-peptides of ESAT-6, CFP-10 and TB7.7 proteins increases the probability that the test covers the broadest range of tissue types and thus gives stronger and more reliable test results in different patient populations.

Wherein the infection is believed to be related to Chlamydia, the antigen or the at least one antigen is selected from the group consisting Serovar D extract, major outer membrane protein (MOMP), cysteine-rich outer membrane proteins (OMPs), OMP2, OMP3, Poly-morphic OMPs (POMPs), adenosine diphosphate/adenosine triphosphate translocase of *Chlamydia pneumonia*, porin B proteins (PorBs), and CT521.

As apparent from the present invention the source of infection may vary. In an embodiment of the present invention the antigen or the at least one antigen is selected from the group consisting of fixed-epimastigotes, fixed-trypomastigotes, disrupted-epimastigotes, disrupted-trypomastigotes, purified antigenic fractions from epimastigotes, semipurified antigenic fractions from epimastigotes, trypomastigote excretory-secretory antigens (TESA), predominant variable antigen type (VAT), variable surface glycoprotein (VSG), trans-sialidase (TS) e.g. TS13, amastigote surface protein-2 (ASP2), KMP-11m, CRA, Ag30, JL8, TCR27, Ag1, JL7, H49, TCR39, PEP-2, Ag36, JL9, MAP, SAPA, TCNA, Ag13, TcD, B12, TcE, JL5, A13, 1F8, Tc-24, Tc-28, Tc-40, Cy-hsp70, MR-HSP70, Grp-hsp78, CEA, CRP, SA85-1.1, FCaBP (flagellar $Ca^{2+}$-binding protein), FL-160 (flagellar surface protein of 160 kDa) and, FRA (flagellar repetitive antigen) said antigens being related to Trypanosomas.

In a preferred embodiment of the present invention the antigen or the at least one antigen is selected from the group consisting of fixed-epimastigotes, fixed-trypomastigotes, disrupted-epimastigotes, disrupted-trypomastigotes, purified antigenic fractions from epimastigotes, semipurified antigenic fractions from epimastigotes, trypomastigote excretory-secretory antigens (TESA), predominant variable antigen type (VAT), variable surface glycoprotein (VSG), trans-sialidase (TS) e.g. TS13, amastigote surface protein-2 (ASP2), FCaBP (flagellar Ca2+-binding protein), FL-160 (flagellar surface protein of 160 kDa) and FRA (flagellar repetitive antigen).

In the case wherein the infection is related to schistosoma, the antigen or at least one antigen is selected from the group consisting of disrupted schistosoma egg, excreted/secreted glycoproteins (ES), tegumental (TG) glycoproteins, soluble egg antigen (SEA), soluble extract of *S. mansoni* (SWAP), keyhole limpet haemocyanin (KLH), RP26, Sj 31, Sj 32, paramyosin, Sm62-IrV5, Sm37-SG3PDH, Sm28-GST, Sm14-FABP, PR52-filamin PL45-phosphoglycerate kinase, PN18-cyclophilin, MAP3, Sm23, MAP4, Sm28-TPI, Sm97, CAA, CCA and, Schistosoma mansoni heat shock protein 70.

In a preferred embodiment of the present invention the antigen or the at least one antigen is selected from the group consisting of excreted/secreted glycoproteins (ES), tegumental (TG) glycoproteins, soluble egg antigen (SEA), soluble extract of S. mansoni (SWAP), keyhole limpet haemocyanin (KLH) and, RP26.

In respect of leishmania, the antigen or at least one antigen is selected from the group consisting of disrupted promastigozyes, leishmanin, rGBP, rORFF, rgp63, rK9, rK26, rK39, PN18-cyclophilin, MAP3, Sm23, MAP4, Sm28-TPI, Sm97, CAA and, CCA.

In fact any antigen specific for the species to be analysed could be useful according to the present invention.

In another preferred embodiment, a range of different antigens from different diseases can be combined to enable a screening tool with low specificity for the individual disease, but high sensitivity for "infection". A kit combining e.g. a palette of antigens from microbes soldiers are exposed to during mission (e.g. malaria, tuberculosis, leishmania, schistosoma and/or trypanosomiasis) will enable doctors to perform one quick screening-test instead of a range of different tests.

In another preferred embodiment, combined kits may comprise of antigens from various microbes infecting an organ (e.g. Nesseria and Chlamydia species causing pelvic inflammatory disease), or comprise of antigens from infectious agents that cause common symptoms (e.g. treatable diarrhoea caused by campylobacter and shigella infection, could be distinguished from untreatable diarrhoea caused by virus e.g. rotavirus).

Subject

Reference to a "subject" includes a human or non-human species including primates, livestock animals (e.g. sheep, cows, pigs, horses, donkey, goats), laboratory test animals (e.g. mice, rats, rabbits, guinea pigs, hamsters), companion animals (e.g. dogs, cats), avian species (e.g. poultry birds, aviary birds), reptiles and amphibians. The present invention has applicability, therefore, in human medicine as well as having livestock and veterinary and wild life applications General Reference to any prior art in this specification is not, and should not be taken as, an acknowledgment or any form of suggestion that this prior art forms part of the common general knowledge in any country.

All patent and non-patent references cited in the present application, are hereby incorporated by reference in their entirety.

As will be apparent, preferred features and characteristics of one aspect of the invention may be applicable to other aspects of the invention. The invention may be embodied in other specific forms without departing from the spirit or essential characteristics thereof. The foregoing embodiments are therefore to be considered in all respects illustrative rather than limiting on the invention described herein. Scope of the invention is thus indicated be the appended claims rather than by the foregoing description, and all changes that come within the meaning and range of equivalency of the claims are intended to be embraced by reference therein.

It should be understood that any feature and/or aspect discussed above in connection with the methods according to the invention apply by analogy to the methods of diagnosis.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention will hereinafter be described by way of the following non-limiting Figures and Examples.

FIGURE LEGENDS

FIG. 1

Correlation between plasma IFN-γ, IP-10, and IFN-γ. Whole blood was stimulated 20-24 hour with either saline (unstimulated) (1a), *M. tuberculosis* specific antigens (1b) or mitogen (1c). Cytokine production was measured in plasma supernatants by ELISA (IFN-y) or multiplex (IP-10).

FIG. 2

Comparison of Antigen-specific IFN-γ and IP-10 cytokine production (i.e. Ag-Nil) measured by Quantiferon ELISA and Luminex respectively. Values are pg/mL. Straight lines represent median values, for range see table 2.

FIG. 3

ROC curve presenting the sensitivity and specificity of the IP-10 assay. The x axis presents 1-specificity, the y-axis the sensitivity.

FIG. 4

A comparison of antigen-specific IP-10 and IFN-γ production. IFN-γ is examined undiluted IP-10 is analysed in 1:8 dilution.

FIG. 5

Antigen-specific IFN-γ and IP-10/CXCL10 production in patients with a negative or indeterminate Quantiferon test Whole blood of 6 Quantiferon in tube (QFT-IT) negative and one QFT-IT indeterminate TB patient was stimulated 20-24 hour with either saline or *M. tuberculosis* specific antigens. Cytokine production was measured in plasma supernatant by ELISA (IFN-γ) and multiplex technology (IP-10). Antigen-specific production represent the antigen stimulated sample subtracted the unstimulated sample. Straight lines represent median values, (Wilcoxon signed rank test).

EXAMPLES

In the following examples the performance of the IP-10 assay is demonstrated using infection with *Mycobacterium tuberculosis* and *Chlamydia Trachomatis* as examples of the test principle General Methods In examples 1-17 we have used whole blood stimulation to demonstrate the principle in example 18 we have used purified blood mononuclear cells (PBMCs).

Whole Blood Stimulation
1. The volume of 1 mL heparinised blood was drawn into three vaccutainer tubes (Cellestis, Australia) coated with
   a. saline, to generate the unstimulated sample or nil sample (used interchangeably)
   b. peptides derived from the proteins ESAT-6, CFP-10 and TB-7.7 to generate the antigen sample (Ag)
   c. phytohaemagluinin (PHA) to generate the mitogen sample.
2. Tubes were incubated 20-24 h at 37° C.
3. Tubes were centrifuged 10 minutes at 2000 rpm
4. Plasma was harvested and frozen at or below −40 C Isolation of Peripheral Blood Mononuclear Cells (PBMCs)
1. PBMCs were separated from whole blood by density gradient centrifugation (Lymphoprep; Nycomed) and frozen in liquid nitrogen until use
2. PBMCs were thawed and re-suspended in RPMI 1640, supplemented with 1% penicillin/streptomycin, 1% nonessential amino acids, 1% glutamine, 1% pyrovat, 1% HEPES, and 10% human AB serum (local blood bank, Rigshospitalet, Copenhagen)
3. The viability and number of cells were determined by nigrosin staining
4. The cells were cultured in triplicate in round-bottom microtiter plates (Nunc) at $1.25 \times 10^5$ cells/well in a total volume of 100 μL Preparation of C. Trachomatis Serovar Strain D Extract Antigen
1. The Chlamydia Trachomatis serovar D strain (UW-3/Cx) was propagated in HeLa 229 cells and fractioned into 30 narrow molecular weight fractions using a multielution technique.
2. C. Trachomatis serovar D in SPG buffer was centrifuged at 30.000 g for 30 min
3. Pellet was re-suspended 1:1 in sterile water and laemmli-reducing sample buffer, followed by boiling for 5 minutes.
4. After repeated sonication, the suspension was centrifuged at 30.000 g for 30 min.
5. The supernatant crude C. Trachomatis serovar strain D extract was used as antigen.

PBMC Stimulation with Serovar D Antigen
1. PBMCs were plated as described above and the cells were stimulated with
   a. 2 μg/mL, serovar D antigen to generate the antigen sample
   b. Without antigen to generate the un-stimulated sample
2. The cells were incubated at 37° C. in humidified air (5% $CO_2$ and 95% air)
3. The supernatants were harvested after 5 days for quantification of IP-10
4. Plasma was harvested and frozen at or below −40 C Biomarker Measurements Luminex:

IP-10 and/or MCP-1 and/or IL-2 were measured on the luminex platform and performed according to the Biosource protocol.
1. Bead suspensions from individual IP-10, IL-2, MCP-2 and/or IFN-γ kits were combined in pre-wetted filter 96 plate wells.
2. The beads were washed twice with wash solution and incubation buffer was added.
3. Samples were diluted 1:1, 1:8 1:10, or 1:20 in assay dilution and 100 μl was added to the plate.
4. The plate was incubated 2 hours at room temperature at 600 rpm on a titer plate shaker.
5. After two washes, 100 μl detection antibody cocktail was added per well, and the plate was incubated at room temperature for one hour on a titer plate shaker.
6. After two washes, 100 μl of strepavidin-RPE solution was added per well.
7. After 30 minutes incubation and three washes, 100 μL of wash solution was added to each well and the plate was placed in the XY platform of the Luminex.
8. From each well, a minimum of 100 analyte specific beads were analyzed for both bead- and RPE fluorescence.

IP-10 ELISA

IP-10 measurements were done using a single step type ELISA from Biosource (Invitrogen, USA).

IFN-γ ELISA

IFN-γ measurements were done using a single step sandwich type ELISA; the Quantiferon IFN-γ ELISA (Cellestis, Australia). Levels of IFN-γ were analyzed using the software provided by the manufacturer (version 2.50). The Cellestis ELISA kit operates in International units (U) (1 Unit/mL corresponds to a concentration of 50 pg/mL) in the present examples we present the ELISA IFN-γ results in pg/ml.

Quantiferon Testing (QFT-IT Test)

IFN-γ production is measured using the Quantiferon ELISA. According to the manufacturers' guidelines, the IFN-γ response of the unstimulated sample is subtracted the IFN-γ response in the sample stimulated with M. tuberculosis-specific antigens and in the mitogen sample. The QTF-IT result was considered "positive" if the response to the specific antigens was ≧17.5 pg/ml (0.35 IU/ml) and ≧25% of the unstimulated value, regardless of the mitogen stimulated IFN-γ response; "negative" if the response to specific antigens was <17.5 pg/ml (0.35 IU/ml) and the mitogen stimulated IFN-γ response was ≧25 pg/ml (0.5 IU/ml). A test was considered "indeterminate" if either both the response to specific antigens was <17.5 pg/ml (0.35 IU/ml) and the mitogen stimulated IFN-γ response was ≦25 pg/ml (0.5 IU/ml); or the IFN-γ response in the unstimulated sample was ≧400 pg/ml (8 IU/ml) regardless of antigen-specific or mitogen stimulated response.

Example 1

High Levels of Plasma IP-10 are Induced by Stimulation of Whole Blood with M. tuberculosis Specific Antigens from Patients Infected with M. tuberculosis We tested whole blood from 12 patients with sputum positive lung tuberculosis from Denmark (n=2) and Guinea Bissau (n=9), and 11 healthy non-TB exposed Danish controls (young doctors, researchers and students from the Department of infectious diseases and clinical research unit at Hvidovre Hospital). No patient was HIV positive. The study was approved by the ethical committee of Copenhagen and Frederiksberg Commune, and the Ethical Committee of Guinea Bissau.

Results

Levels of IFN-γ and IP-10 (median values and range) in the plasma of whole blood samples incubated with Nil, Ag or Mitogen, measured by Luminex IP-10, Luminex IFN-γ or the commercial Quantiferon-IFN-γ ELISA are presented in table 1.

Production of IP-10 after incubation with M. tuberculosis specific antigens is strongly associated with the presence of an infection with M. tuberculosis in the patient; Very high levels of IP-10 in the plasma, 1025 pg/ml (range: 497.3-2080.4 pg/ml), of whole blood culture were induced during stimulation with M. tuberculosis specific antigens in patients infected with M. tuberculosis whereas, very low levels of IP-10 40.4 pg/ml (range: 19.7-158.8) were seen in whole blood culture of the 11 healthy Danish individuals with no known exposure or signs of infection with M. tuberculosis (controls). The difference between the two groups was highly significant; p<0.0001 showing that IP-10 release is indeed antigen induced.

The amount of antigen stimulated IP-10 of 1024 pg/ml (range 497-2080 pg/ml) was significantly higher than the levels of IFN-γ determined by ELISA of 223.5 (99-1283 pg/ml) and Luminex 90.7 pg/ml (37-464 pg/ml) (p=0.01 and 0.001)

Compared with IP-10, significantly lower plasma levels of IFN-γ were determined by Qunatiferon-ELISA, but the difference between TB infected and non-TB infected was still significant. IFN-γ measured by Luminex were even lower than IFN-γ measured by the QFT-IFN-γ ELISA and will therefore not be discussed further.

In conclusion, IP-10 is a highly specific marker for infection with M. tuberculosis when whole blood from an infected person is stimulated with M. tuberculosis specific antigens. IP-10 is much easier to measure and has great potential as a more sensitive marker due to the high levels released.

TABLE 1

IFN-γ and IP-10 production in whole blood culture.

IFN-γ and IP-10 production (pg/ml)$^a$ in plasma of saline, antigen, or mitogen stimulated whole blood from:

| | Controls (n = 11) | TB patients (n = 12) |
|---|---|---|
| | IFN-γ (ELISA) | |
| Saline | 8.5 (6.5-11.5) | 10.3 (6.5-134.5) |
| Antigens | 8.9 (5.0-14.0) | 223.5 (99.0-1283.0)$^b$ |
| Mitogen | 1613.0 (45.5-1798.5) | 272.8 (31.5-1750.5) |

TABLE 1-continued

IFN-γ and IP-10 production in whole blood culture.

IFN-γ and IP-10 production (pg/ml)$^a$ in plasma of saline, antigen, or mitogen stimulated whole blood from:

| | Controls (n = 11) | TB patients (n = 12) |
|---|---|---|
| | IFN-γ (Multiplex) | |
| Saline | 5.0 (5.0-11.5) | 5.0 (5.0-70.2) |
| Antigens | 5.0 (5.0-11.8) | 90.7 (37.3-464.2)$^b$ |
| Mitogen | 291.9 (5.0-2980.7) | 160.9 (5.0-2913.4) |
| | IP-10 | |
| Saline | 27.1 (17.7-140.6) | 150.9 (61.1-991.9)$^c$ |
| Antigens | 40.4 (19.7-158.8) | 1025 (497.3-2080.4)$^b$ |
| Mitogen | 993.5 (164.0->2800) | 843.0 (384.4-2587.9) |

Whole blood was stimulated 20-24 hours with saline (unstimulated), M. tuberculosis specific antigens or mitogen. Cytokine production was measured by ELISA (IFN-γ) and multiplex (IFN-γ, IP-10).
$^a$Values are median (range).
$^b$Significantly different (P < 0.0001).
$^c$Significantly different (P < 0.0005).
$^d$Significantly different (P < 0.008). Kruskal-Wallis test

Example 2

Elevated Spontaneous IP-10 Release in Plasma of Unstimulated Whole Blood Culture (Nil Sample) from Patients with Active TB Infection; IP-10 as a Marker for Active Disease As seen from table 1, patients with active tuberculosis had 5.6 fold higher plasma levels of IP-10 in unstimulated whole blood samples (nil) (150.9 pg/ml (61.1-991.9)) compared to healthy controls (27.1 pg/ml (17.7-140.6)) p=0.0005. There was no significant difference in plasma nil IP-10 between patients with active tuberculosis from Guinea Bissau and Denmark (p=0.67).

In conclusion: This indicates that determination of spontaneous IP-10 release in combination with antigen stimulated IP-10 release can be used to discriminate healthy individuals from patients with active TB,

Example 3

Correlation Between IFN-γ and IP-10 Release

There is a strong correlation between IFN-γ and IP-10 release in whole blood culture, but IP-10 release is of higher magnitude. Individual responses to IP-10 after nil, antigen or mitogen stimulation and the corresponding ELISA IFN-γ are shown in FIG. 1a-c. There was a strong correlation between the levels of IP-10 and ELISA IFN-γ in the plasma of antigen stimulated whole blood (spearman r=0.87, 95% C.I 0.71 to 0.95, p<0.0001) (FIG. 1b) and in the plasma of mitogen stimulated whole blood, though not at the same level (r=0.54, 95% C.I. 0.15 to 0.78, p=0.008 (FIG. 1c).

In conclusion: IP-10 and IFN-γ release in whole blood culture correlates, but IP-10 release is of higher magnitude. This makes IP-10 a better marker than IFN-γ in in-vitro TB tests.

Example 4

Figure 2:
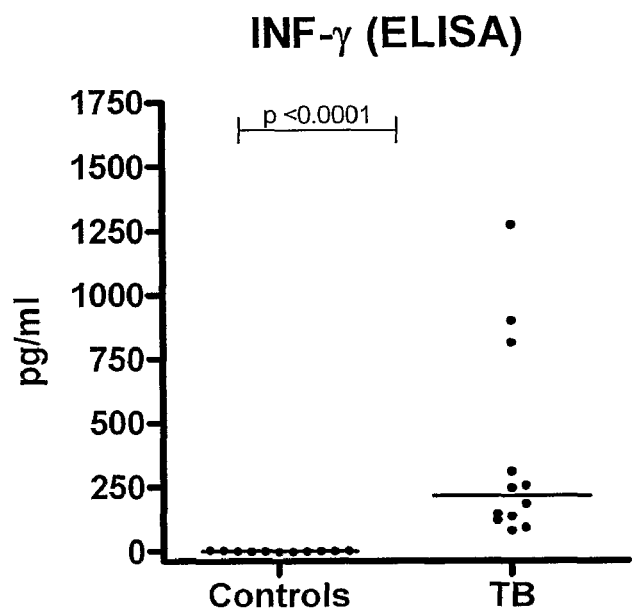
Figure 2:
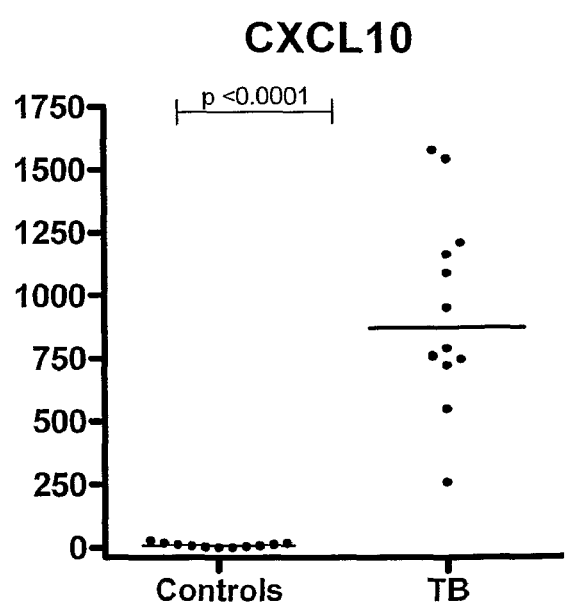

Antigen-Specific IP-10 Production is Higher than Antigen-Specific IFN-γ Production To determine the amount cytokine released in response to the antigens present in the culture (i.e. the antigen-specific (Ag-specific) cytokine response). The antigen-specific cytokine response was calculated as a delta value (=cytokine production in antigen stimulated whole blood culture subtracted by the amount released into plasma of un-stimulated whole blood culture). The delta value allows us to compare the antigen-specific IFN-γ and IP-10 cytokine production. As seen in FIG. 2, the IP-10 assay measures higher values of Ag-specific IP-10 (870.4 pg/ml (260.5-1575.9 pg/ml)) compared to Ag-specific IFN-γ (216.5 pg/ml (80.5-1273.0 pg/ml) ) p=0.006 (Mann-Whitney). Median values and ranges are presented in table 2.

In conclusion: IP-10 is released in higher amounts (p=0.006) is thus easier to measure and seems a better marker than IFN-γ.

TABLE 2

Comparison of Ag-specific INF-γ and IP-10 cytokine production measured by Quantiferon ELISA and Luminex respectively (Kruskal-Wallis test).

|  | Controls (n = 11) | TB (n = 12) | P-values |
|---|---|---|---|
| INF-γ, Quantiferon Elisa (pg/ml) | | | |
| Ag-Nil, median (range) | −0.5 (−3.5-3.5) | 216.5 (80.5-1273.0) | <0.0001 |
| IP-10, Luminex (pg/ml) | | | |
| Ag-Nil, median (range) | 10.8 (1.1-27.6) | 870.4 (260.5-1575.9) | <0.0001 |

Example 5

Very High Sensitivity and Specificity of the IP-10 Assay

Figure 3:
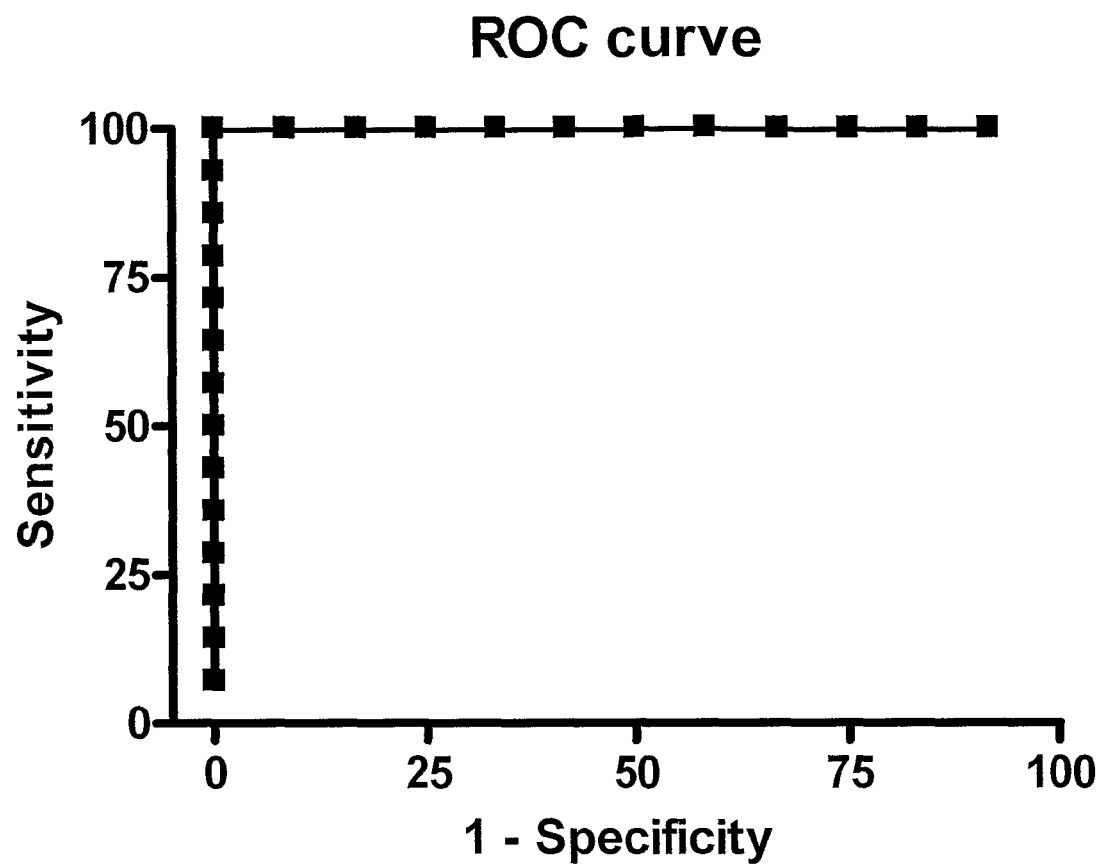

Very high sensitivity and specificity of the IP-10 assay is demonstrated using TB as an example of the test principle. The high sensitivity and specificity of the IP-10 assay described in the invention is determined using a ROC curve analysis based on levels of Antigen-specific IP-10 (antigen-stimulated subtracted nil) values. The present ROC curve analysis is based on the 12 TB patients and 11 healthy controls described in example 1, In FIG. 3 we demonstrate that the IP-10 test segregates perfect between patients with active tuberculosis and healthy controls. In this experiment the IP-10 test has an Area Under the Curve (AUC) of 1.0.

Conclusion: the IP-10 assay used in the diagnosis of infection with *M. tuberculosis* was shown to be 100% sensitive and 100% specific, which is a better performance than the currently used in vitro TB tests. The IP-10 test is here clearly able to discriminate between patients with and without tuberculosis infection. Based on this limited material it possible to set the cut-off between 27.6 pg/ml and 260.5 pg/ml and achieve complete segregation.

Example 6

IP-10 is an Efficient Marker for Latent TB in Immunosuppressed

Whole blood from six patients with Rheumatoid arthritis (RA) receiving corticosteroids and methotrexate© were stimulated with nil, one *M. tuberculosis* specific antigen (ESAT6), or mitogen (PHA). IP-10 concentration was measured in the supernatant using Luminex as described above. Patient 1-3 were known Quantiferon test negative and Patient 4-6 were Quantiferon test positive.

As seen in table 3, all patients, despite immune suppression, mounted high levels of IP-10 in response to the positive mitogen control. High levels of ESAT6 stimulated IP-10 (range 668-2800 pg/ml) were observed in all patients with latent TB (positive Quantiferon test). In conclusion, the IP-10 based test can be used for the diagnosis of latent TB infection in patients with immune-suppression.

TABLE 3

Six patients with Rheumatoid arthritis were stimulated with nil, ESAT-6 (one of the antigens used in the Quantiferon test), or mitogen. IP-10 was measured by Luminex.

| Patient | QFT test | Nil | ESAT6 | Mitogen |
|---|---|---|---|---|
| 1 | − | 35 | 184 | 1141 |
| 2 | − | 87 | 95 | 2800 |
| 3 | − | 38 | 47 | 2800 |
| 4 | + | 34 | 2800 | 1589 |
| 5 | + | 63 | 1605 | 2800 |
| 6 | + | 31 | 668 | 1393 |

The upper three patients are Quantiferon test negative and the lower three are Quantiferon test positive. All patients are free of active TB disease symptoms but suffering from and under massive immunosuppressive medication for severe RA (candidates to biologic treatment i.e. TNF-α blockers).

Example 7

IP-10 as Marker for Latent TB in Healthy Persons with Known TB Exposure in Youth Two test persons (RV and AKA) with known TB exposure in youth, proven PPD conversion and no tuberculosis chemoprophylaxis and no co-morbidities were tested for IP-10 responsivity using the method described in above. The donors were known to be Quantiferon positive from previous tests. Both test persons reacted with strong antigen (ESAT-6) specific IP-10 responses (302.9 pg/ml and 916.1 pg/ml) see in table 9. The test person RV has been tested twice 2 months apart, there is good reproduction of results (data not shown).

In conclusion: IP-10 is a strong as marker for latent tuberculosis infection.

TABLE 4

Two healthy patients with known TB exposure in youth are tested for tuberculosis antigen responsivity (ESAT6).

| Patient | QFT test | Nil | Ag (ESAT6 stimulation only) | Mitogen |
|---|---|---|---|---|
| AKA | + | 22.5 | 325.4 | 631 |
| RV | + | 10.4 | 926.5 | 491.5 |

Example 8

The Level of Spontaneous IP-10 in a Sample in Combination with Antigen-Specific IP-10 Release, can Distinguish Healthy with or without Latent TB Infection from Patients with Active TB In example 6 (table 3) we showed that spontaneous (nil) IP-10 levels are low in both latently tuberculosis infected 34 pg/ml (range 31-63 pg/ml)) and not-infected (38 pg/ml (range 35-87 pg/ml)) patients with rheumatoid arthritis. These levels were at a similarly low level as that seen in un-infected healthy donors (27.1 pg/ml (range 17.7-140.6 pg/ml), table 1) and latently infected donors (22.5 and 10.4 pg/ml), table 4.). If we pool all patients without active tuberculosis and compare these low levels to the high levels of spontaneous IP-10 release seen in patients with active TB (150.9 pg/ml (range 61.1-991.9)) (table 1) we find a highly significant difference (p<0.0001, Mann Whitney).

In conclusion, the combination of spontaneous and antigen-specific IP-10 release can be used to discriminate between active and latent tuberculosis infection.

Example 9

Dilution of Plasma Samples can be Done without Losing the Sensitivity of the IP-10 Test Dilution of sample is a stepwise lowering of concentrations by addition of a diluting solution. We have tested if dilution of a plasma sample after incubation, interferes with the fold relation between plasma samples with high and low IP-10 concentration, and if this dilution interferes with the sensitivity of the IP-10 assay. Samples were diluted in assay dilution provided the Biosource Luminex kit.

As seen from table 5, dilution of the samples results in a stepwise lowering of the Ip-10 levels in plasma of antigen and mitogen stimulated whole blood and plasma of unstimulated (nil) whole blood.

TABLE 5

Plasma from nil, antigen and mitogen stimulated whole blood was dilutet 1:2-1:16 in assay dilution and analysed for IP-10 levels using Luminex.

|  | Dilution factor | IP-10 Patient A | Patient B |
|---|---|---|---|
| Nil | 1:2 | 22.5 | 10.4 |
|  | 1:4 | 11.7 | 5.2 |
|  | 1:8 | 4.4 | 2.9 |
|  | 1:16 | 1.3 | 1.3 |
| Antigen | 1:2 | 631 | 491 |
|  | 1:4 | 430 | 327 |
|  | 1:8 | 396 | 197 |
|  | 1:16 | 277 | 130 |
| Mitogen | 1:2 | 325 | 927 |
|  | 1:4 | 225 | 541 |
|  | 1:8 | 139 | 438 |
|  | 1:16 | 89 | 326 |

In table 5 we see that the antigen-specific IP-10 concentration remains very high even in the samples diluted 16 fold (275 pg/ml and 128 pg/ml).

Figure 4:
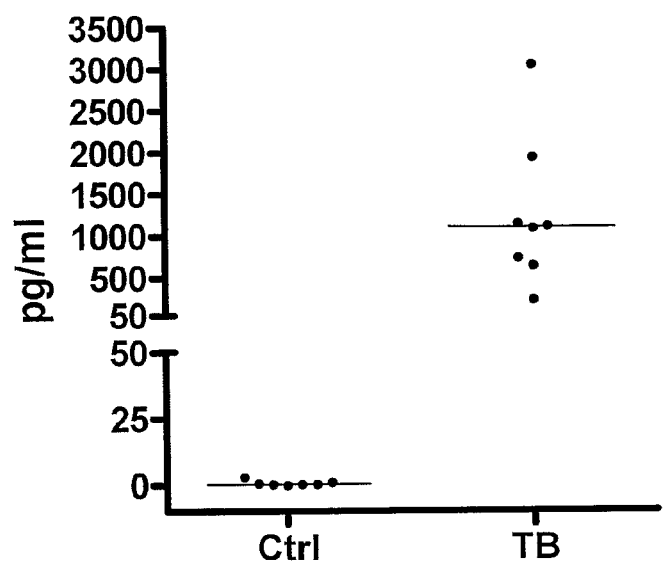
Figure 4:
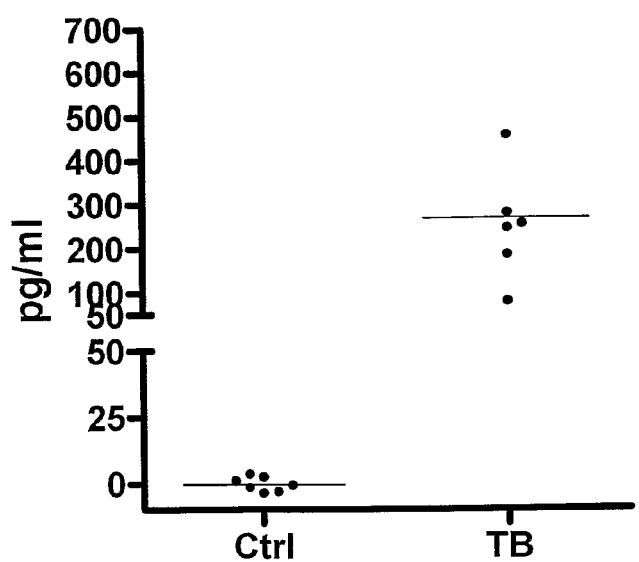

FIG. 4 presents data from 7 controls and 8 tuberculosis patients tested for antigen-specific IFN-γ and IP-10 responses. The antigen-specific IP-10 production is measured following 1:8 times dilution of the sample and the IFN-γ response is measured in the undiluted sample. Again we found highly specific IP-10 values indicating that IP-10 is a strong marker for *M. tuberculosis* infection (p=0.0003) even at 1:8 times dilution. Furthermore diluted 1:8 the IP-10 values (median 1097 pg/ml (range 225-3045 pg/ml)) are higher compared to the IFN-γ analysed on undiluted sample material (median 269 pg/ml (range 81-1273 pg/ml)) p=0.014 (Wilcoxon matched pairs test).

These results demonstrate that IP-10 is a very robust marker for a diagnostic assay and that The IP-10 test can be used in a test setup where the sample material is very scarce. This opens up for a whole range of applications of the IP-10 test, where the sample can be diluted (either before or after incubation) in cases where only very little sample material is available (directly applicable in e.g. in a commercial product for infants with very low blood volume)

In conclusion: it is demonstrated that plasma samples can be diluted without losing the sensitivity of the IP-10 test.

Example 10

Figure 5:
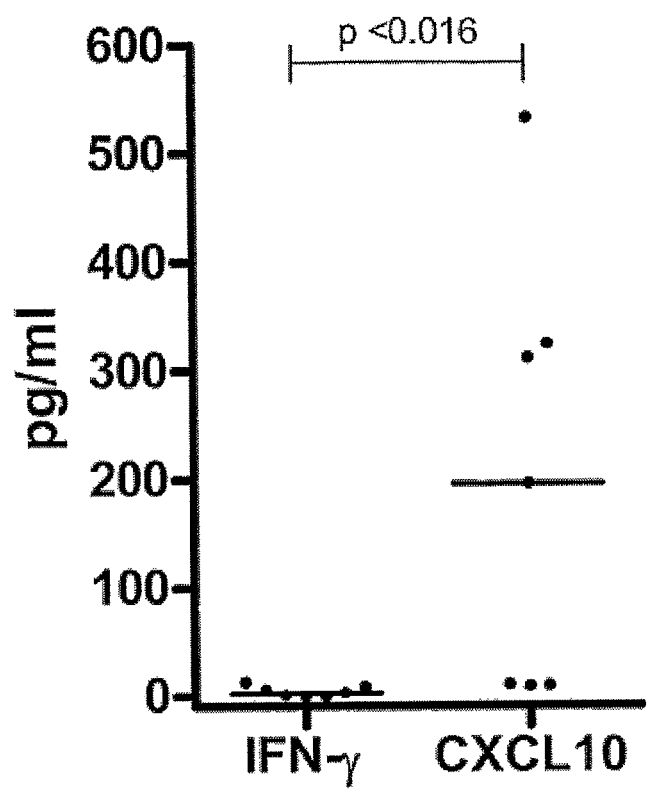

IP-10 is more Sensitive than IFN-γ and Improves in Vitro Diagnosis of Tuberculosis Infection To explore if IP-10 had the potential to improve sensitivity of the current QFT-IT test, we tested the IP-10 responses in tuberculosis patients with negative or indeterminate QFT-IT test results, (for patient characteristics and individual measurements see table 6). These patients were in other words false negative in the IFN-γ test. FIG. 5 shows the antigen-specific IP-10 and IFN-γ responses in 7 patients with TB and a negative or indeterminate QFT-IT test. The antigen-specific IFN-γ responses, determined by QFT-IT ELISA, ranged from 0-12.8 pg/ml whereas, the antigen-specific IP-10 responses ranged from 0-532 pg/ml. Of the 7 patients, 3 were also IP-10 unresponsive with an antigen-specific response below 10 pg/ml, whereas the other 4 patients responded with a median IP-10 level of 318 pg/ml (range 196-532 pg/ml). Of the 4 patients with a negative QFT-IT test and positive IP-10 response, 2 were HIV co-infected with a CD4 cell count of 32 cells/µl and 300 cells/µl respectively. The mitogen specific IP-10 release was high in all donors ranging from 394 to 2800 pg/ml. These surprising findings underline the increased sensitivity of IP-10 based in vitro tests compared to IFN-γ based tests.

TABLE 6

Table 6. Patients with active TB and negative or indeterminate QFT-IT test result were tested for IP-10 responsiveness.

| Donor no. | Country[a] | Age (years) | Diagnosis[b] | Microscopy/ culture | HIV | CD4 (cells/µl) | IFN-γ (pg/ml)[c] | | | QFT-IT result[d] | IP-10 (pg/ml)[c] | | | IP-10 result[e] |
|---|---|---|---|---|---|---|---|---|---|---|---|---|---|---|
| | | | | | | | Saline | Antigens | Mitogen | | Saline | Antigens | Mitogen | |
| 1 | GB | 50 | pTB | +/n.d.[g] | pos | 300 | 8 | 7 | 32 | neg | 72 | 383 | 520 | Pos |
| 2 | GB | 45 | pTB | +/n.d. | pos | 333 | 13 | 13 | 596 | neg | 97 | 106 | 757 | Neg |
| 3 | GB | 50 | pTB | +/n.d. | pos | n.d. | 7 | 10 | 1446 | neg | 98 | 107 | 2800 | Neg |
| 4 | DK | 39 | epTB | +/+ | pos | 767 | 3 | 2 | 1051 | neg | 29 | 39 | 2800 | Neg |
| 5 | DK | 36 | pTB | +/+ | neg | n.d. | 38 | 44 | 249 | neg | 716 | 1040 | 2800 | Pos |
| 6 | DK | 41 | pTB | +/+ | n.d. | n.d. | 7 | 20 | 291 | neg | 31 | 227 | 556 | Pos |
| 7 | DK | 26 | epTB | +/+ | pos | 32 | 20 | 28 | 30 | ind.[h] | 301 | 834 | 394 | Pos |

[a]GB—Guinea Bissau; DK—Denmark
[b]pTB—pulmonary TB, epTB—extrapulmonary TB
[c]Whole blood was stimulated 20-24 hour with either saline, *M. tuberculosis* specific antigens (ESAT-6, CFP10, and TB 7.7) or mitogen (PHA). Cytokine production was measured by ELISA (IFN-γ) and multiplex (IP-10).
[d]A positive QFT-IT response was defined as an antigen-specific response of 17.5 pg/ml above nil according to the manufacturer guidelines.
[e]A positive IP-10 response was defined as an antigen-specific IP-10 response of 36 pg/ml above nil arbitrarily based on the mean results of 11 healthy controls + 3 standard deviations (patients from example 4)
[g]n.d.—not done
[h]Indeterminate

Example 11

Strong Antigen-Specific IP-10 Responses can be Generated at Short and Long Incubation In table 7 we present the un-stimulated and antigen stimulated responses from a typical TB patient examined at 6-120 h incubation. As can be seen from table 7 it is possible to induce IP-10 responses with antigen stimulation, at very short incubation time. >1 ng is produced at 6 h and very high responses 3-6 ng are maintained during 120 hours incubation. These findings demonstrate that the performance of the IP-10 test is very robust and can be performed at very short (<6 h) and very long incubation times

TABLE 7

Un-stimulated (saline) and antigen-stimulated responses from a typical TB patient examined at 6-120 h incubation.

| TIME | IP-10 (pg/ml) | |
|---|---|---|
| Hours | Saline | Antigens |
| 6 | 93 | 1173 |
| 12 | 117 | 3467 |
| 24 | 93 | 5467 |
| 48 | 96 | 5867 |
| 120 | 80 | 6133 |

Example 12

Strong Antigen-Specific IP-10 Responses can be Generated at a Range of Incubation Temperatures As can be seen from table 8 it is possible to induce IP-10 responses with antigen-stimulation at wide range of temperatures. >200 pg/ml antigen-specific IP-10 is produced at 30° C., indicating that incubation below 30° C. is possible, and that incubation at temperatures in the range of e.g. 30-37° C. will generate strong antigen-specific responses.

TABLE 8

Un-stimulated and antigen-stimulated responses from a typical TB patient examined at 24 h incubation at 20-37° C.

| Temperature (° C.) | Saline | Antigens |
|---|---|---|
| 20.0 | 8 | 6 |
| 30.0 | 4 | 221 |
| 37.0 | 5 | 852 |

IP-10 values are in pg/ml

Example 13

Small Amounts of Whole Blood can be Diluted Before Incubation and Still Generate Strong IP-10 Responses Samples of 1 ml (1:0), 0.5 ml (1:1) and 0.1 ml (1:10) whole blood was diluted in RPMI-1640 to a total volume of 1 ml. Diluted whole blood was stimulated in QFT-IT tubes 24 h. Values are not corrected for dilution factor. As can be seen from table 9 it is possible to dilute whole blood in RPMI-1640 before incubation and still generate antigen-specific IP-10 responses >80 pg/ml. This indicates that further dilution is possible and a test kit using very small amounts of blood or cells can be developed.

TABLE 9

. Un-stimulated and antigen-stimulated responses from a typical TB patient using small aliquots of whole blood diluted in RPMI-1640.

| Dilution | N | A |
|---|---|---|
| 1:0 | 93 | 5467 |
| 1:1 | 40 | 2933 |
| 1:10 | 13 | 93 |

IP-10 levels are in pg/ml

Example 14

IP-10 Stability at 25 C

Aliquots of plasma from PHA stimulated whole blood from four donors were stored at 25 C for ½ h, 1 h, 2 h, 4 h, 8 h, or 24 h before analysis. From table 10 it is evident that IP-10 is a very stable molecule that does not disintegrate even at 24 h at 25 C.

TABLE 10

Tabel 10. IP-10 stability at 25 C. (measurements are in pg/ml).

| | | Donor 1 | Donor 2 | Donor 3 | Donor 4 |
|---|---|---|---|---|---|
| Time at 25 C. | 0 h | 63 | 769 | 482 | 127 |
| | ½ h | 57 | 649 | 471 | 115 |
| | 1 h | 72 | 754 | 461 | 116 |
| | 2 h | 68 | 728 | 438 | 115 |
| | 4 h | 62 | 727 | 487 | 126 |
| | 8 h | 66 | 693 | 459 | 137 |
| | 24 h | 77 | 763 | 455 | 149 |

Example 15

IP-10 Stability at 5 C.

Aliquots of plasma from PHA stimulated whole blood from four donors were stored at 5 C for 12 h, 24 h, 72 h, 144 h, or 216 h (9 days) before analysis. From table 11 it is evident that IP-10 is a very stable molecule that does not disintegrate even at 216 h (9 days) at 5 C.

TABLE 11

Table 11. IP-10 stability at 5 C.

| | | Donor 1 | Donor 2 | Donor 3 | Donor 4 |
|---|---|---|---|---|---|
| Time at 5 C. | 0 h | 63 | 769 | 482 | 127 |
| | 12 h | 71 | 646 | missing | 134 |
| | 1 d | 69 | 664 | 501 | 144 |
| | 3 d | 78 | 784 | 539 | 166 |
| | 6 d | 81 | 883 | 495 | 187 |
| | 9 d | 93 | 728 | 520 | 183 |

Example 16

IP-10 Stability at Freeze Thaw Cycles

Aliquots of plasma from PHA stimulated whole blood from four donors were frozen (−80 C) and thawed up to ×5 before analysis. From table 12 it is evident that IP-10 is a very freeze/thaw stable molecule that does not disintegrate even at ×5 freeze-thaw cycles.

TABLE 12

Table 12. IP-10 freeze-thaw stability

|  |  | Donor 1 | Donor 2 | Donor 3 | Donor 4 |
|---|---|---|---|---|---|
| Freeze | x0 | 63 | 769 | 482 | 127 |
| thaw | x1 | 66 | 879 | 388 | 131 |
| cycles | x2 | 74 | 793 | 513 | 122 |
|  | x3 | 70 | 795 | 486 | 126 |
|  | x4 | 65 | 952 | 459 | 126 |
|  | x5 | 80 | 746 | 483 | 142 |

Example 17

IP-10 as a Diagnostic Biomarker is Platform-Independent.

IP-10 levels are not only measurable using Luminex, in example 17 we have measured samples from 4 patients with active TB and 4 healthy controls using ELISA technology (Biosource).

As can be appreciated from table 13 all four patients produce antigen-specific IP-10 above 457 pg/ml whereas the controls all produce IP-10 below 13 pg/ml.

TABLE 13

Antigen-specific IP-10 production from 4 controls and 4 patients measured by ELISA technology.

|  | Antigen-specific IP-10 (pg/ml) |
|---|---|
| Control 1 | 9 |
| Control 2 | 13 |
| Control 3 | 0 |
| Control 4 | 0 |
| Patient 1 | 457 |
| Patient 2 | 626 |
| Patient 3 | 719 |
| Patient 4 | 620 |

Example 18

Combining Measurements of IP-10 and Other Known Biomarkers to Create a Stronger Combined Marker, and Increase the Number of Positive Responders For unknown reasons some individuals respond strong with one biomarker and not another following antigen challenge. For example some individuals may not show either IP-10 or IFN-γ responses, or only produce only low levels of IP-10 or IFN-γ. In this case simultaneous measurement of the two, three, four or more biomarkers will increase sensitivity of the assay and increase the number of positive responders. By combining IP-10 and e.g. IFN-γ measurements it is therefore possible to make diagnostic predictions that are less vulnerable to single biomarker anergy.

One approach to this combined biomarker strategy is seen in table 15 where the IP-10 and Quantiferon results from table 6 are combined to the following matrix: if the patient react positive to at least one of the tests, then the patient is considered infected. In the presented example there are no negative QFT-IT responders that are positive by IP-10 test.

TABLE 14

| Patient nr | QFT-IT result | IP-10 result | Combined QFT-IT/IP-10 result |
|---|---|---|---|
| 1 | neg | Pos | Pos |
| 2 | neg | Neg | Neg |
| 3 | neg | Neg | Neg |
| 4 | neg | Neg | Neg |
| 5 | neg | Pos | Pos |
| 6 | neg | Pos | Pos |
| 7 | ind. | Pos | Pos |

Table. QFT-IT and IP-10 test results are combined and interpreted as if a patient is positive by at least one test then the patient is considered infected. Cut point for IP-10 test was defined as an antigen-specific IP-10 response of 36 pg/ml above nil, arbitrarily based on the mean results of 11 healthy controls + 3 standard deviations (patients from example 4), Another more complex method of constructing a combined biomarker is seen in table 16. Antigen-specific IP-10 and IFN-γ responses are combined by addition and by multiplication. Seven un-exposed controls and 8 patients with active TB were evaluated. From table 14 we see the median and range of antigen-specific IP-10 and IFN-γ responses; and the median and range of added and multiplied IP-10 and IFN-γ responses. By addition the span between highest responding control and lowest responding patient is increased from 62 pg/ml for IFN-γ, and 1727 pg/ml for IP-10, to 1863 pg/ml, and by multiplication to $164642(pg/ml)^2$. This surprising stark increase in span by multiplication, also increased the relative fold difference based on the mean to a staggering 379274 fold, this is compared to the antigen-specific IP-10 which had 619 fold differences between patients and controls, or IFN-γ who had 1074 fold difference.

TABLE 15

Table 15. Antigen specific IP-10 and antigen-specific IFN-γ was added or multiplied to construct a combines IP-10/IFN-γ biomarker.

|  |  | Antigen-Specific IP-10 | Antigen-Specific IFN-γ | Addition | Multiplication |
|---|---|---|---|---|---|
| Controls | Median | 0 | 0 | 2 | 2 |
| n = 7 | Min | 0 | 0 | 0 | 0 |
|  | Max | 63 | 2 | 62 | 62 |
| Patients | Median | 8779 | 215 | 9074 | 2019761 |
| n = 8 | Min | 1800 | 64 | 1865 | 164704 |
|  | Max | 24355 | 1018 | 25373 | 25146884 |

Antigen-specific measurements <0 were normalized to 0,

Example 19

Diagnosis of Chlamydia Trachomatis Infection Using the IP-10 Assay

PBMC were isolated from 7 patients with Chlamydia trachomatis infection and from 7 donors with no recorded history of Chlamydia infection. PBMCs were stimulated in 5 day culture and supernatants were analysed for IP-10 production using luminex and IFN-γ production using ELISA.

From table 16 we see that high levels (>0.5 ng/ml) of PBMC culture supernatant IP-10 are induced by stimulation with Clamydia Trachomatis serovar D extract antigen in patients suffering from Chlamydia trachomatis genital infection. It is evident that some controls respond to this unspecific stimulation, but that the levels are lower. There is high antigen specific IP-10 production >0.5 ng/ml.

In conclusion IP-10 is a novel diagnostic biomarker for Chlamydia infection.

TABLE 16

Table 16. Nil, antgen and antigen-specific levels of
IP-10 and IFN-γ were induced in PBMC 5 day culture.

|  |  | IP-10 (pg/ml) | | | IFN-γ (pg/ml) | | |
|---|---|---|---|---|---|---|---|
|  |  | Nil | Ag | Ag specific | Nil | Ag | Ag specific |
| Controls | Control 01 | 0 | 252 | 252 | 128 | 2184 | 2056 |
|  | Control 10 | 45 | 14 | −31 | 148 | 146 | −2 |
|  | Control 18 | 226 | 820 | 594 | 0 | 474 | 474 |
|  | Control 20 | 282 | 998 | 716 | 4 | 2514 | 2510 |
|  | Control 25 | 66 | 1240 | 1175 | 30 | 296 | 266 |
|  | Control 28 | 0 | 2 | 2 | 40 | 112 | 72 |
|  | Control 31 | 10 | 4 | −6 | 84 | 162 | 78 |
|  | Median | 45 | 252 | 252 | 40 | 296 | 266 |
| Patients | Patient 01 | 14 | 2472 | 2458 | 0 | 7808 | 7808 |
|  | Patient 03 | 2 | 1449 | 1446 | 84 | 2976 | 2892 |
|  | Patient 04 | 498 | 3725 | 3227 | 10 | 8206 | 8196 |
|  | Patient 05 | 13 | 1317 | 1304 | 36 | 7516 | 7480 |
|  | Patient 12 | 21 | 4707 | 4686 | 0 | 10214 | 10214 |
|  | Patient 18 | 1 | 503 | 502 | 4 | 6264 | 6260 |
|  | Patient 02 | 58 | 1680 | 1621 | 10 | 4016 | 4006 |
|  | Median | 14 | 1680 | 1621 | 10 | 7516 | 7480 |

REFERENCES

Abramo C, Meijgaarden K E, Garcia D, Franken K L, Klein M R, Kolk A) et al. Monokine induced by interferon gamma and IFN-gamma response to a fusion protein of Mycobacterium tuberculosis ESAT-6 and CFP-10 in Brazilian tuberculosis patients. Microbes Bourgarit, A., G. Carcelain, V. Martinez, C. Lascoux, V. Delcey, B. Gicquel, E. Vicaut, P. H. Lagrange, D. Sereni, and B. Autran. 2006. Explosion of tuberculin-specific Th1-responses induces immune restoration syndrome in tuberculosis and HIV co-infected patients. AIDS 20: F1-F7.

Hughes, A. J., P. Hutchinson, T. Gooding, N. J. Freezer, S. R. Holdsworth, and P. D. Johnson. 2005. Diagnosis of Mycobacterium tuberculosis infection using ESAT-6 and intracellular cytokine cytometry. Clin. Exp. Immunol. 142:132-139.

Pai, M., R. Joshi, S. Dogra, D. K. Mendiratta, P. Narang, S. Kalantri, A. L. Reingold, J. M. Colford Jr, L. W. Riley, and D. Menzies. 2006. Serial Testing of Health Care Workers for Tuberculosis using Interferon-γ Assay. Am. J. Respir. Crit Care Med.

The invention claimed is:

1. A method for diagnosing an infection caused by Mycobacteria comprising:
   a) incubating a sample comprising T-cells obtained from a human with at least one Mycobacteria specific peptide or protein test-antigen under the proviso that said test-antigen is not PPD,
   b) determining the test-antigen specific cell-mediated immune response by measuring the IP-10 level in said sample,
   c) comparing the determined IP-10 level with a reference-level, and
   d) classifying said human as one that is likely to be infected with at least one Mycobacteria, if the determined IP-10 level is equal to or above the reference level or classifying said human as one that is unlikely to be infected with at least one Mycobacteria, if said determined IP-10 level is below the reference level.

2. The method according to claim 1, wherein the infection is an active infection, or a latent infection.

3. The method according to claim 1, wherein the Mycobacteria is selected from the group consisting of *M tuberculosis* complex organisms, Mycobacteria where the region of difference (RD1) has not been deleted and Mycobacteria pathogenic to humans.

4. The method according to claim 1, wherein the Mycobacteria specific peptide or protein test-antigen is selected from the group consisting of RD-1 antigens, ESAT-6, CFP10, TB7.7, Ag 85 and HSP-65.

5. The method according to claim 1, wherein the sample is derived from blood.

6. The method according to claim 1, wherein the sample is whole blood.

7. A method for diagnosing an infection caused by Mycobacteria comprising:
   a) incubating a first fraction of a sample comprising T-cells obtained from a human with at least one Mycobacteria specific peptide or protein test-antigen to generate a response sample, under the proviso that said test-antigen is not PPD,
   b) incubating a second fraction of the sample with an inactive solution to generate a nil sample,
   c) determining the IP-10 levels in the two fractions,
   d) determining the test-antigen dependent cell-mediated immune response by subtracting the IP-10 level determined in the nil sample from the IP-10 level determined in the response sample,
   e) comparing the test-antigen dependent cell-mediated immune response or a value derived thereof with a reference-level or a value derived thereof, and
   f) classifying said human as one that is likely to have an infection if said determined test-antigen specific cell-mediated immune response level is equal to or above the reference level or a value derived thereof or classifying said human as one that is unlikely to have an infection if said determined test-antigen specific cell-mediated immune response level is below the reference level or a value derived thereof.

8. The method according to claim 7, wherein a third fraction of the sample is incubated with a T-cell activator to generate a positive control.

* * * * *

UNITED STATES PATENT AND TRADEMARK OFFICE
CERTIFICATE OF CORRECTION

| | | |
|---|---|---|
| PATENT NO. | : 8,026,076 B2 | Page 1 of 3 |
| APPLICATION NO. | : 12/438515 | |
| DATED | : September 27, 2011 | |
| INVENTOR(S) | : Morten Ruhwald et al. | |

It is certified that error appears in the above-identified patent and that said Letters Patent is hereby corrected as shown below:

At title page 1, Item 74, Line 1, Change "Knobber" to --Knobbe--.

In the Specifications:

In Column 2, Line 10, Change "immunosupressing" to --immunosuppressing--.
In Column 2, Line 16, Change "infection" to --infection.--.
In Column 2, Line 38, Change "is was" to --it was--.
In Column 2, Line 63, Change "simltaneously" to --simultaneously--.
In Column 2, Line 67, Change "(men)" to --(men).--.
In Column 3, Lines 13-14, Change "disease," to --disease.--.
In Column 3, Line 22, Change "Encephalopaties)" to --Encephalopathies)--.
In Column 3, Line 40, Change "pheripheral" to --peripheral--.
In Column 4, Line 31, Change "antigens" to --antigens.--.
In Column 5, Line 62, Change "TRF-assaýs," to --TRF-assays,--.
In Column 5, Line 66, Change "cromatographic" to --chromatographic--.
In Column 6, Line 63, Change "polymere" to --polymer--.
In Column 7, Line 39, Change "1O)," to --10),--.
In Column 9, Line 3, Change "cytometri" to --cytometry--.
In Column 10, Line 50, Change "biomarker" to --biomarker.--.
In Column 11, Line 3, Change "biomarker" to --biomarker.--.
In Column 11, Line 25, Change "biomarker" to --biomarker.--.
In Column 12, Line 34, Change "leishmanina" to -- leishmania,--.
In Column 12, Line 41, Change "Phthirius" to --Phthirus--.
In Column 12, Lines 45-46, Change "Campylobactor," to --Campylobacter,--.
In Column 12, Line 47, Change "bacteri" to --bacteria--.
In Column 12, Lines 57-58, Change "Creutzfelt-Jacob" to --Creutzfeldt-Jakob--.
In Column 13, Line 30, Change "broncoscopy," to --bronchoscopy,--.
In Column 14, Line 35, Change "leptospir," to -- leptospirae,--.
In Column 14, Line 35, Change "Clamydia," to --Chlamydia,--.

Signed and Sealed this
Twenty-first Day of May, 2013

Teresa Stanek Rea
*Acting Director of the United States Patent and Trademark Office*

CERTIFICATE OF CORRECTION (continued)   Page 2 of 3
U.S. Pat. No. 8,026,076 B2

In Column 14, Line 39, Change "Ebstein" to --Epstein--.
In Column 14, Line 41, Change "varicellea-zoster" to --varicella zoster--.
In Column 14, Line 44, Change "cariini" to --carinii--.
In Column 15, Line 61, Change "Celsius" to --Celsius.--.
In Column 16, Line 17 (Approx.), Change "aspitate" to --aspirate--.
In Column 16, Line 36, Change "aspitate," to --aspirate,--.
In Column 16, Line 46, Change "alliquots" to --aliquots--.
In Column 16, Line 64, Change "Alliquots" to --Aliquots--.
In Column 16, Line 66, Change "900 µl ," to --900 µl,--.
In Column 17, Line 1, Change "1900µl ," to --1900 µl,--.
In Column 17, Line 6, Change "vaccutainer-tube" to --vacutainer-tube--.
In Column 18, Line 30, Change "result)" to --result).--.
In Column 20, Line 50, Change "deviation)" to --deviation).--.
In Column 21, Line 36, Change "immunocromatographic" to --immunochromatographic--.
In Column 24, Line 2, Change "histocompatability" to --histocompatibility--.
In Column 27, Line 18, Change "cytometri." to --cytometry.--.
In Column 27, Line 52, Change "strepavidin-RPE" to --streptavidin-RPE--.
In Column 28, Line 47, Change "organims," to --organisms,--.
In Column 28, Line 48, Change "viroids" to --viroids.--.
In Column 28, Line 50, Change "Mycobactiera," to --Mycobacteria,--.
In Column 28, Line 53, Change "Clamydia," to --Chlamydia,--.
In Column 28, Line 54, Change "Ebstein" to --Epstein--.
In Column 28, Line 59, Change "cariini" to --carinii--.
In Column 28, Line 64, Change "Mycobactiera," to --Mycobacteria,--.
In Column 28, Line 65, Change "Clamydia, Tryphanosomasis" to --Chlamydia, Trypanosomiasis--.
In Column 29, Line 5, Change "M. lepra)" to --M. leprae)--.
In Column 29, Line 12, Change "and or" to --and/or--.
In Column 29, Line 57, Change "state" to --state.--.
In Column 31, Lines 56-57, Change "promastigozyes," to --promastigotes,--.
In Column 32, Line 21, Change "applications" to --applications.--.
In Column 33, Line 27, Change "principle" to --principle.--.
In Column 33, Line 34 (Approx.), Change "vaccutainer" to --vacutainer--.
In Column 33, Line 40, Change "phytohaemagluinin" to --phytohaemagglutinin--.
In Column 33, Line 52, Change "pyrovat," to --pyruvate,--.
In Column 34, Line 37 (Approx.), Change "strepavidin-RPE" to --streptavidin-RPE--.
In Column 35, Line 43 (Approx.), Change "0.001)" to --0.001).--.
In Column 35, Line 45 (Approx.), Change "Qunatiferon-ELISA," to --Quantiferon-ELISA,--.
In Column 36, Line 40, Change "TB," to --TB.--.
In Column 37, Line 8, Change "pg/ml)" to -- pg/ml))--.
In Column 39, Line 19 (Approx.), Change "dilutet" to --diluted--.
In Column 40, Line 14 (Approx.), Change "volume)" to --volume).--.
In Column 41, Line 14 (Approx.), Change "times" to --times.--.
In Column 42, Line 24 (Approx.), Change "Tabel" to --Table.--.

CERTIFICATE OF CORRECTION (continued)
U.S. Pat. No. 8,026,076 B2

In Column 44, Line 14 (Approx.), Change "4)," to --4).--.
In Column 44, Line 46, Change "0)," to --0).--.
In Column 44, Line 61 (Approx.), Change "Clamydia" to --Chlamydia--.
In Column 45, Line 2 (Approx.), Change "antgen" to --antigen--.

In the Claims:

In Column 46, Line 12-13 (Approx.), In Claim 3, change "M tuberculosis" to --M. tuberculosis--.